(12) United States Patent
Hudson et al.

(10) Patent No.: US 11,692,070 B2
(45) Date of Patent: Jul. 4, 2023

(54) ADDITIVE MANUFACTURING SUPPORT MATERIAL

(71) Applicant: Carnegie Mellon University, Pittsburgh, PA (US)

(72) Inventors: Andrew Hudson, Pittsburgh, PA (US); Thomas Hinton, Pittsburgh, PA (US); Adam Feinberg, Pittsburgh, PA (US); Andrew Lee, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 669 days.

(21) Appl. No.: 16/603,158

(22) PCT Filed: Apr. 5, 2018

(86) PCT No.: PCT/US2018/026293
§ 371 (c)(1),
(2) Date: Oct. 4, 2019

(87) PCT Pub. No.: WO2018/187595
PCT Pub. Date: Oct. 11, 2018

(65) Prior Publication Data
US 2020/0032004 A1 Jan. 30, 2020

Related U.S. Application Data

(60) Provisional application No. 62/606,578, filed on Sep. 28, 2017, provisional application No. 62/601,949, filed on Apr. 5, 2017.

(51) Int. Cl.
| | | |
|---|---|---|
| C08L 1/00 | (2006.01) | |
| C08L 89/00 | (2006.01) | |
| C08G 61/04 | (2006.01) | |
| C08J 3/075 | (2006.01) | |
| B33Y 70/00 | (2020.01) | |
| C09D 11/04 | (2006.01) | |
| B29C 64/40 | (2017.01) | |

(52) U.S. Cl.
CPC ............. *C08J 3/075* (2013.01); *B33Y 70/00* (2014.12); *C09D 11/04* (2013.01); *B29C 64/40* (2017.08); *C08J 2389/00* (2013.01); *C08J 2389/04* (2013.01)

(58) Field of Classification Search
CPC ........ A61L 27/52; A61L 27/50; A61L 27/222; A61L 27/20; A61L 27/24; C08J 3/075; C08J 2389/04; C08J 2389/00; B33Y 70/00; B33Y 80/00; B29C 64/40; C09D 11/04; C08L 5/04
USPC ............................. 106/135.1, 124.1; 520/1
See application file for complete search history.

(56) References Cited

U.S. PATENT DOCUMENTS

| | | | |
|---|---|---|---|
| 2,800,457 A | 7/1957 | Green et al. | |
| 3,242,051 A | 3/1966 | Heistand et al. | |
| 3,748,227 A | 7/1973 | Wagner et al. | |
| 4,428,869 A | 1/1984 | Munteanu et al. | |
| 6,294,204 B1 | 11/2001 | Rossling et al. | |
| 2003/0065400 A1 | 4/2003 | Beam et al. | |
| 2003/0193102 A1* | 10/2003 | Yan ......................... | B01J 13/10 264/4.1 |
| 2016/0167312 A1* | 6/2016 | Feinberg ................. | A61L 27/10 264/239 |

FOREIGN PATENT DOCUMENTS

| | | |
|---|---|---|
| CN | 105796478 | 7/2016 |
| CN | 106039411 | 10/2016 |
| CN | 106039414 | 10/2016 |
| CN | 205903442 | 1/2017 |
| CN | 107614264 | 1/2018 |
| EP | 0316054 | 5/1989 |
| JP | S5871879 | 4/1983 |
| JP | 2018-500894 | 1/2018 |
| WO | WO 2016/090286 | 6/2016 |

OTHER PUBLICATIONS

Jieying et al., "Theory and Practice of Modern Physical Pharmacy", Shanghai Science and Technology Literature Press, Apr. 2005, 7 pages (with machine translation).
Ruzhi, "Pharmacy", People's Health Press, Oct. 2000, pp. 353-356, 12 pages (with machine translation).
PCT International Preliminary Report on Patentability in International Appln. No. PCT/US2018/026293, dated Oct. 8, 2019, 8 pages.
Database WPI Week 198323 Thomson Scientific, London, GB; AN 1983-55015K XP002798522, & JP S58 71879 A (Snow Brand Milk Prod Co Ltd) Apr. 28, 1983 (Apr. 28, 1983) (abstract).
EP Supplementary Search Report in European Appln. No. 18780662. 5, dated Apr. 9, 2020, 11 pages.
Abbadessa, "Thermosensitive hydrogels for 3D bio printing of cartilage constructs," Dissertation, Urecht Institute for Pharmaceutical Science, 2017, 219 pages.
Gelatin-GMIA.com [online] "The Gelatin Handbook," 1896, retrieved on Oct. 4, 2019, retrieved from URL: <http://www.gelatingmia.com/uploads/1/1/8/4/118450438/gmia_gelatin_manual_2019.pdf, 3 pages.

(Continued)

*Primary Examiner* — Jessica Whiteley
(74) *Attorney, Agent, or Firm* — Fish & Richardson P.C.

(57) ABSTRACT

This document describes a process of producing gel microparticles, which are consistent in size and morphology. Through the process of coacervation, large volumes of gel microparticle slurry can be produced by scaling up reactor vessel size. Particles can be repeatedly dehydrated and rehydrated in accordance to their environment, allowing for the storage of particles in a non-solvent such as ethanol. Gel slurries exhibit a Bingham plastic behavior in which the slurry behaves as a solid at shear stresses that are below a critical value. Upon reaching the critical shear stress, the slurry undergoes a rapid decrease in viscosity and behaves as a liquid. The rheological behavior of these slurries can be adjusted by changing the compaction processes such as centrifugation force to alter the yield-stress. The narrower distribution and reduced size of these particles allows for an increase in FRESH printing fidelity.

22 Claims, 21 Drawing Sheets

(56) References Cited

OTHER PUBLICATIONS

Hinton et al., "Three-dimensional printing of complex biological structures by freeform reversible embedding of suspended hydrogels," Science advances, 2015, 1:e1500758.
Lemetter et al., "Control of the morphology and the size of complex coacervate microcapsules during scale-up," Process Systems Engineering, 2009, 55:1487-1496.
Mohanty et al., "Microscopic structure of gelatin coacervates," International journal of biological macromolecules, 2005, 36:39-46.
PCT International Search Report and Written Opinion in International Appln. No. PCT/US2018/26293, dated Jun. 13, 2018, pp. 49.
Hinton, "Rapid Prototyping Tissue Models of Mammary Duct Epithelium," Thesis for the degree of Doctor of Philosophy in Biomedical Engineering, Carnegie Mellon University, Apr. 2017, 144 pages.

* cited by examiner

US 11,692,070 B2

ADDITIVE MANUFACTURING SUPPORT MATERIAL

CLAIM OF PRIORITY

This application is a 35 U.S.C. § 371 National Stage Application of PCT/US2018/026293, filed Apr. 5, 2018, which, in turn, claims the benefit of priority under 35 U.S.C. § 119(e) to U.S. Patent Application Ser. No. 62/601,949, filed on Apr. 5, 2017, and Application Ser. No. 62/606,578, filed Sep. 28, 2017, the entire contents of each of which are hereby incorporated by reference.

GOVERNMENT SUPPORT CLAUSE

This invention was made with government support under the National Institutes of Health No. HL117750. The government has certain rights in this invention.

TECHNICAL FIELD

This application relates to additive manufacturing, specifically to a support material for additive manufacturing.

BACKGROUND

Additive manufacturing can be used to create three dimensional objects or structures. A material can be printed into a support scaffolding that temporarily supports the structure during assembly. When assembly is completed, the support scaffold is removed.

SUMMARY

This application describes a support material for additive manufacturing, and processes for manufacturing thereof. A process for additively manufacturing fluids called Freeform Reversible Embedding of Suspended Hydrogels (FRESH) includes embedding a fluid material (e.g., alginate, collagen, fibrin, etc.) into a fugitive support material (e.g., comprising a microparticle slurry). The support material and processes for producing the support material described below overcome limitations imposed by the traditional mechanical blending techniques for producing a support material. The support material described below includes microparticles of approximately uniform size and uniform geometry. For additive manufacturing processes (e.g., embedded printing in the support material), the support material enables generation of printed structures that have a higher fidelity (e.g., fewer defects, fewer voids, fewer irregularities, etc.) in the printed structure than printed structures using prior versions of support materials.

The process for providing the support material described below is more efficient than prior processes to create polymeric micro and nanogels for drug encapsulation and/or delivery use the underlying chemical principles of emulsification or coacervation. Prior processes can include blending and emulsion. These prior processes are less efficient with lower yield, creating particles in small volumes and rely on chemicals and polymers that are less suitable for bioprinting.

Described herein are processes to create a support material including microparticles, which overcome the limitations of traditional mechanical blending techniques for generating particles of support materials. By using a scalable phase separation known as coacervation, large quantities of monodisperse microparticles can be manufactured from a variety of raw, reversibly gelling materials with tight control over particle morphology and bulk rheological behavior. Phase separation is utilized to drive the formation of gel particles. These particles can then be further isolated to form a support material. By embedding a gelling fluid "ink" in this support material, inks are allowed to fuse into three-dimensional objects.

These processes rely on dissolving a gel in a mixture of a solvent (such as water) and co-solvent (such as ethanol) under stirring. By altering mixing conditions, the gel's solubility decreases until gel particles nucleate out of solution. These particles can be washed and isolated to form a support material slurry.

This process creates gel microparticles in a simple, single-step, high-yield and inexpensive manner. Due to its chemically driven nature, this process is also easily scalable to large volumes, which is difficult for other processes, which rely on mechanical blending, emulsification, or ultracentrifugation. This process allows for the large-scale production of support material to enable the rapid adoption of 3D printing gelling fluids.

The support material includes a slurry including a solution and coacervate particles in the solution, the coacervate particles being of substantially uniform geometries; where at least a portion of the slurry forms a rigid body when experiencing a stress below a threshold stress; and where at least a portion of the slurry forms a viscous fluid when experiencing a stress above the threshold stress.

In some implementations, the solution comprises a surfactant configured to reduce a number of dendritic coacervate particles that form in the solution relative to a number of the dendritic coacervate particles that form in a solution without the surfactant. In some implementations, the coacervate particles each comprises at least one of gelatin, alginate, and cellulose. In some implementations, the coacervate particles comprise two or more different polymers. In some implementations, one of the two or more different polymers comprises gum arabic, and where another of the two or more different polymers comprises gelatin. In some implementations, the solution comprises one or more of water and ethanol.

In some implementations, a harmonic mean size of the coacervate particles is between about 0.5 μm and about 60 μm. In some implementations, a harmonic mean size of the coacervate particles varies less than about 35%.

In some implementations, the threshold stress comprises a critical shear stress in which a cohesive force between first and second of the coacervate particles of the slurry is approximately equal to an external shear force applied to the coacervate particles of the slurry. In some implementations, a value of the critical shear stress is between about 20 Pa and about 140 Pa. A value of the critical shear stress is based on a viscosity of an ink for additive manufacturing in the slurry. In some implementations, the ink comprises collagen.

This document describes processes for producing the support material, the processes including generating coacervate from a polymer, the coacervate including particles that are substantially uniform in geometry, where generating the coacervate comprises: forming a solution of a solvent and a co-solvent; stirring the solution and dissolving the polymer into the solution; and adjusting a pH of the solution to a particular value based on a type of the polymer; and forming, from the coacervate, a slurry with a particular yield-stress value, the forming including compacting the coacervate during one or more centrifugation cycles.

In some implementations, the process includes selecting one or more parameters, and modulating the one or more parameters during generation of the coacervate, each of the one or more parameters including: a gelatin bloom value, a polymer processing method, a polymer precipitation rate, a polymer solubility, a molecular weight of the polymer, a polymer concentration, a volume ratio of the solvent and the co-solvent, a surfactant type, a surfactant concentration, a cooling rate, or a stirring rate.

In some implementations, the process includes selecting one or more parameters; and modulating the one or more parameters during the forming of the slurry, the one or more parameters including: a type of the washing solution, a centrifugation time of the one or more centrifugation cycles, a centrifugation force of the one or more centrifugation cycles, and a number of the one or more centrifugation cycles.

In some implementations, the polymer is a gelatin including a gelatin bloom value of one of 200 bloom, 250 bloom, and 275 bloom. The polymer is a gelatin, and where the gelatin comprises one or both of an acid-cured gelatin or a lime-cured gelatin. The solution comprises a ratio of solvent to co-solvent of about 52.5:47.5, where the solvent comprises water, and where the co-solvent comprises ethanol.

In some implementations, the process includes adding a surfactant to the solution. The actions include dehydrating the slurry in ethanol. In some implementations, the process includes rehydrating the slurry in water, where the slurry maintains the particular yield-stress value after dehydration and rehydration.

In some implementations, the polymer is a first polymer, and generating the coacervate further comprises: adding a second polymer to the solution, selecting an isoelectric point of either the first polymer or the second polymer, and adjusting the pH based on the selected isoelectric point. In some implementations, the first polymer comprises gelatin, the second polymer comprises gum arabic, and the pH is about 5-6.

In some implementations, the process includes adjusting the one or more centrifugation cycles to cause the particular yield-stress value of the slurry to be a specified value. In some implementations, the specified value is between about 20 Pa and about 140 Pa. In some implementations, the specified value is based on a viscosity of an ink for additive manufacturing in the slurry.

In some implementations, the ink comprises collagen. In some implementations, the process includes washing the coacervate in a washing solution. In some implementations, the coacervate particles are approximately monodisperse in the solution.

In some implementations, the support material includes a gelatin slurry including: a colloid solution including ethanol and water; a surfactant; and coacervate microparticles in the colloid solution, the coacervate microparticles being monodisperse in the solution, the coacervate microparticles having mean sizes between 0.5-60 micrometers and a variance of size of less than 35%; where at least a portion the slurry forms a rigid body when experiencing a shear stress below a yield-stress value; and where at least a portion of the slurry forms a viscous fluid when experiencing a shear stress above the yield-stress value.

The details of one or more embodiments of the support material are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

Figure 1A:
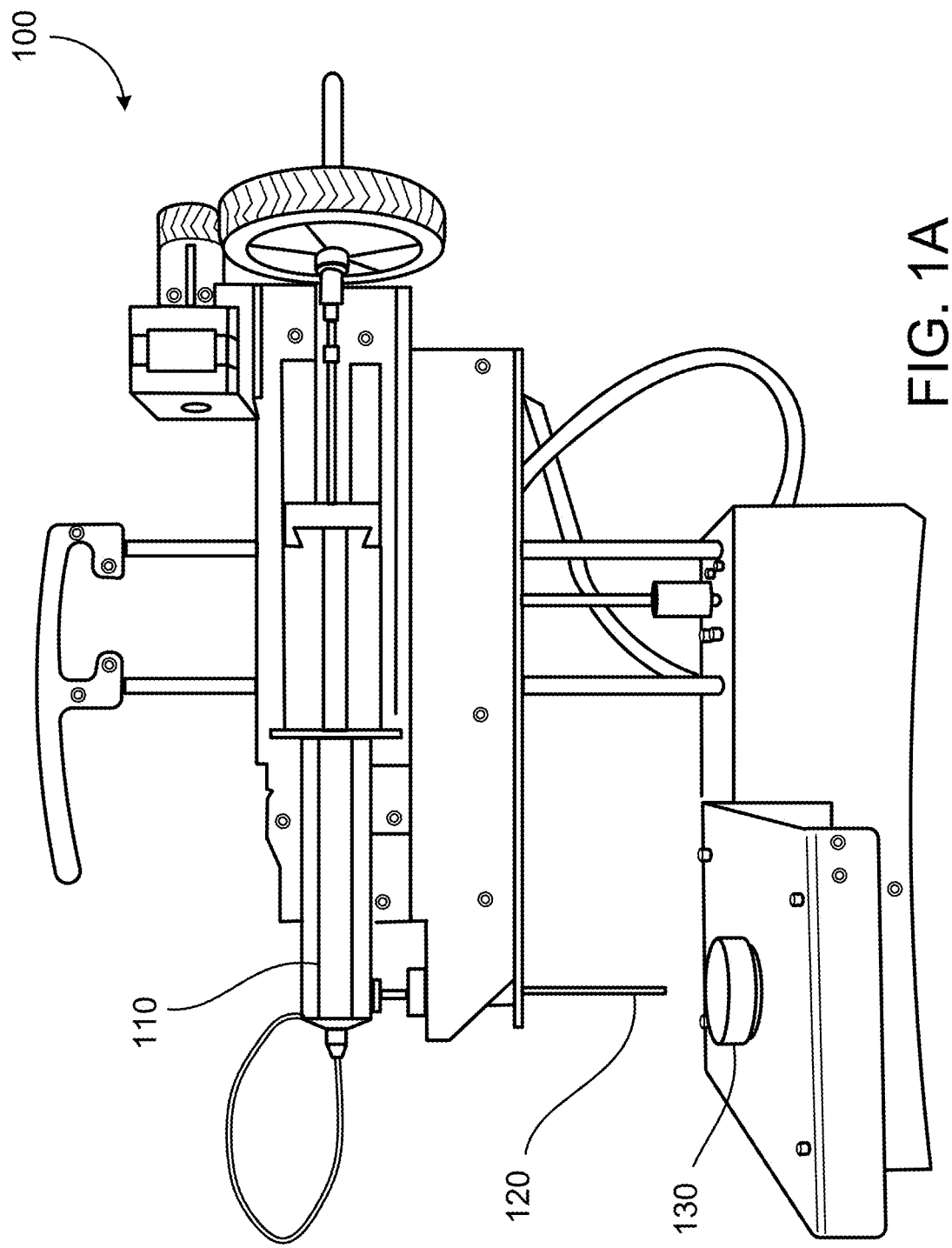
FIG. 1A shows a printing system.

FIG. 1A shows a printing system 100. The printing system 100 is configured to print a material 110 (e.g., collagen, fibrin, etc.) embedded into a support material 130, such as through an injector 120. The support material 130 forms a scaffold to support the material 110 while printing is conducted and while the material hardens (e.g., while gelation occurs). When the viscosity and yield-stress of the support material 130 are similar to the printed material (also referred to as an ink), the printing system 100 can print with greater precision than when the viscosity and yield-stress of the support material do not match or are not similar to those of the support material. Further, a support material that forms a slurry with smaller particles facilitates high-fidelity printing of a structure in the support material by the printing system 100.

The support material 130 includes a material that forms a scaffold support for additive manufacturing processes. The support material includes a slurry that supports embedded materials (e.g., inks) used in embedded 3D printing of structures. The support material supports the printed ink embedded in the support material temporarily. Once the structure has been formed by the printing process, the support material is removed.

The support material (also referred to as a support bath) exhibits at least some of the properties of a Bingham plastic. For example, the support material exhibits the properties of a solid material when the support material is not experiencing a stress (e.g., a shear stress) that is above a yield-stress value. A least a portion of the support material behaves like a viscous liquid when the portion of the support material experiences a stress (e.g., a shear stress) above the yield-stress value. In some implementations, a printer injector applies the stress to the support material as it moves through the support material. This enables the printer head to inject ink into the support material, which supports the ink in place until the structure has been formed. The ink may include tissues such as collagen, or other materials, such as materials that undergo gelation after being injected into the support material. The support material supports the ink until gelation is completed. The support material can then be removed (e.g., melted away).

The yield-stress of the support material is an important factor in enabling precise form factors to be printed in the support material. The homogeneity of the support material is also a factor in the quality of the printed structure. The support material described herein can have a yield-stress that is set to be a particular value (e.g., based on the application, type of ink, etc.). The support material described herein includes particles of particular sizes, which are designed to increase printing fidelity and enable precise 3D embedded printing of structures.

Figure 1B:
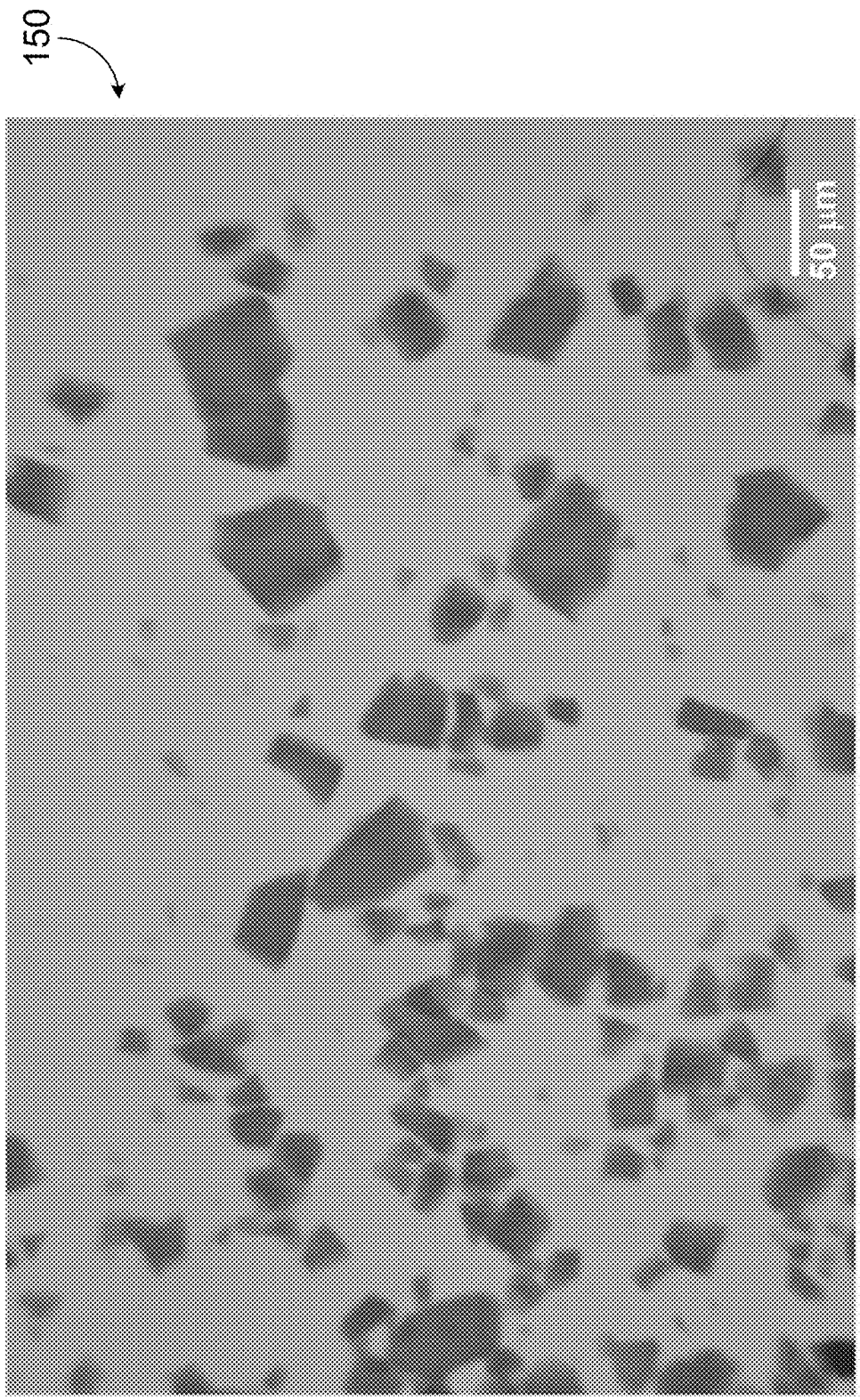
FIG. 1B shows a representation of gelatin particles.

FIG. 1B shows an example of a gelatin support material 150 produced by blending techniques. This example shows generation of gelatin microparticle support utilized mechanical blending of gelatin blocks to produce smaller gelatin particles. Due to the nature of the blending process, the gelatin microparticles produced were random in both their size and shape distributions. The support material 150 shows particles having irregular sizes and shapes. These particles are not evenly dispersed in a support bath slurry. For embedded printing applications, approximately uniform particle size, shape, and dispersal is preferred. The support material and processes for producing the support material described below overcome or reduce limitations imposed by the traditional mechanical blending techniques for producing a support material. The support material described below includes microparticles of approximately uniform size and uniform geometry. For additive manufacturing processes (e.g., embedded printing in the support material), the support material enables generation of printed structures that are of higher fidelity (e.g., fewer defects, voids, irregularities, etc.) in the printed structure than printed structures using prior versions of support materials. As shown in FIG. 1B, gelatin microparticles 150 produced by mechanical blending show random size and shape distribution. The scale bar is 50 microns.

FIGS. 2-6 show representations of example support materials 200, 300, 400, 500, and 600 produced by a coacervation process. Particles produced by the coacervation process are smaller and more consistent in morphology, relative to the support material 150 shown in FIG. 1B, which is produced by a mechanical blending process.

The base material that forms the particles of the support material includes a polymer. The polymer can include one or more of gelatin, alginate, cellulose, and similar polymers. The base material undergoes a coacervation process to generate a coacervate including the material. The coacervate includes microparticles of the material of substantially uniform geometry. The particles having substantially uniform geometry have substantially the same shape, dimensions, configuration, and arrangement, especially uniformity between the particles. For example, the particles have substantially uniform size. Here, substantially uniform size is meant that particles (e.g., droplets) exhibit a particle size distribution having a coefficient of variance (i.e., the standard deviation of the population divided by the population mean) of less than about 35% or about 10, 15, 20, 25, or about 30%. A coefficient of variation of less than about 15% is preferred. In some embodiments, about 70 percent, or about 90 percent, of the beads possess a volume particle diameter from about 0.90 to about 1.1 times the average volume particle diameter of the particles. In some implementations, the particles are monodisperse in the coacervate.

The coacervate support synthesis protocol for forming a support material for embedded printing applications includes coacervation of the material and compaction of the material. The parameters of the support material can be selected based on the particular application of the support material (e.g., based on the ink to be used in an embedded printing process). These parameters (size, yield, etc.) affect the yield-stress of the support material. The yield-stress of the support material is based on the sizes of the particles produced during the coacervate process, and can be tuned to a particular value. The properties of the base material (e.g., a polymer) can be selected and/or modulated to tune the size of the coacervate particles and thus the yield-stress of the support material. The properties can include the type of base material, processing method of the material, precipitation rate of the polymer (e.g., during coacervation), polymer solubility, molecular weight of the material, polymer concentration, volume ratio of the solution (e.g., solvent to co-solvent), surfactant type, surfactant concentration, cooling rate, and a stirring rate.

The coacervation of the support material follows the example process below. An ethanol-water solution is created. The base material to be used (e.g., gelatin, alginate, cellulose, etc.) is measured out. The amount of the material dissolved in the solution can be set to vary the size and yield of the particles of the support material. The heating rate and cooling rate can affect the precipitation rate of the polymer into the solution, which will affect particle size. The rate of mixing also affects particle size, as described in further detail below. For example, faster mixing rates cause the precipitate particles to be smaller in average size. Size of the particles can be measured as a harmonic mean size, as described above. While the base material (e.g., polymer) is dissolved, a surfactant can be added and dissolved into the solution. Once the polymer is dissolved, the pH of the solution can be reduced (e.g., by adding acid) until the isoelectric point of the polymer is reached, and the polymer begins to precipitate into the solution. The solution is stirred until the polymer precipitation is completed or substantially completed such that the solution represents a coacervate.

The coacervate solution is compacted to form the support material. The coacervate solution is put in a centrifuge. The number of centrifuge cycles, duration, speed (e.g., RPM setting), and other centrifuge settings are based on the desired yield-stress of the support material, the amount of coacervate, the polymer being used, and so forth. After the coacervate is compacted, it is washed in a washing solution. The type of washing solution being used can depend on the material that is to be printed in the support material (e.g., collagen, alginate, etc.).

Below is an example process for preparing the support material. A solution is prepared by measuring a 50:50 ethanol-water solution. The ratio of ethanol to water can be adjusted to tune the particle size of the support material. For example, the ratio can include 47.5:52.5 ethanol to water, or similar ratios. For example, 500 mL deionized (DI) water can be used, and 500 mL 200 proof, anhydrous ethanol (EtOH) can be used for a 50:50 ratio. For a gelatin-based support material, 20 g type B gelatin (2 wt %) and 2.5 g F127 pluronic (0.25 wt %) surfactant are measured. The 500 mL DI water is heated to 45° C. The warm water is mixed into the EtOH container. While stirring, the gelatin and pluronic powders are slowly added. Sufficient time (e.g. about ten minutes) can be allowed for the gelatin and the pluronic powders to fully dissolve in the solution. While stirring, the pH of the solution is adjusted down to 5.6-5.7 with an acid (e.g.,-1M HCl). Turbidity of the solution is indicative of coacervation. At this stage, the stirring speed is increased to at least 500 RPM. The stirring speed should be high enough to avoid pulling air bubbles into solution.

Below are example steps for completing preparation of the support material. The "raw" coacervate solution is placed in a centrifuge. For example, the support material can be put in the centrifuge tubes for about 2 minutes at 175 G. The supernatant is removed. A yellow-white pellet of gelatin at the bottom of the container is left in the tube, and the tube is refilled with the raw coacervate solution. The loose pellet is broken up (e.g., by shaking the container). The solution is centrifuged, e.g., for two minutes at 175 G. The supernatant is removed. A 2:1 ratio of DI to gelatin is added. The pellet is dispersed to break up any clumps. The solution is centrifuged, e.g., for two minutes at 225 G. The supernatant is removed and replaced with 1X PBS with 25 mM HEPES solution. The solution is centrifuged, e.g., for two minutes at 450 G. The solution forms a gelatin slurry, which should begin to swell as it becomes more neutral through washing. A swelling ratio may be as high as 3:1.

In some implementations, if printing alginate, the supernatant is replaced with DI water. The solution is centrifuged, e.g., for two minutes at 450 G. The supernatant is removed and a washing fluid is added. For alginate printing, the washing fluid can include 0.16 wt % $CaCl_2$. Fibrin and collagen printing can use other washing solutions. In some implementations, the slurry can be refrigerated. In some implementations, additional centrifuging can be performed, e.g., for two minutes at 450 G. In some implementations, a vacuum chamber can be used for 20-30 minutes. In some implementations, additional centrifuging can be done, e.g., for five minutes at 750 G. The supernatant is removed.

Figure 2:
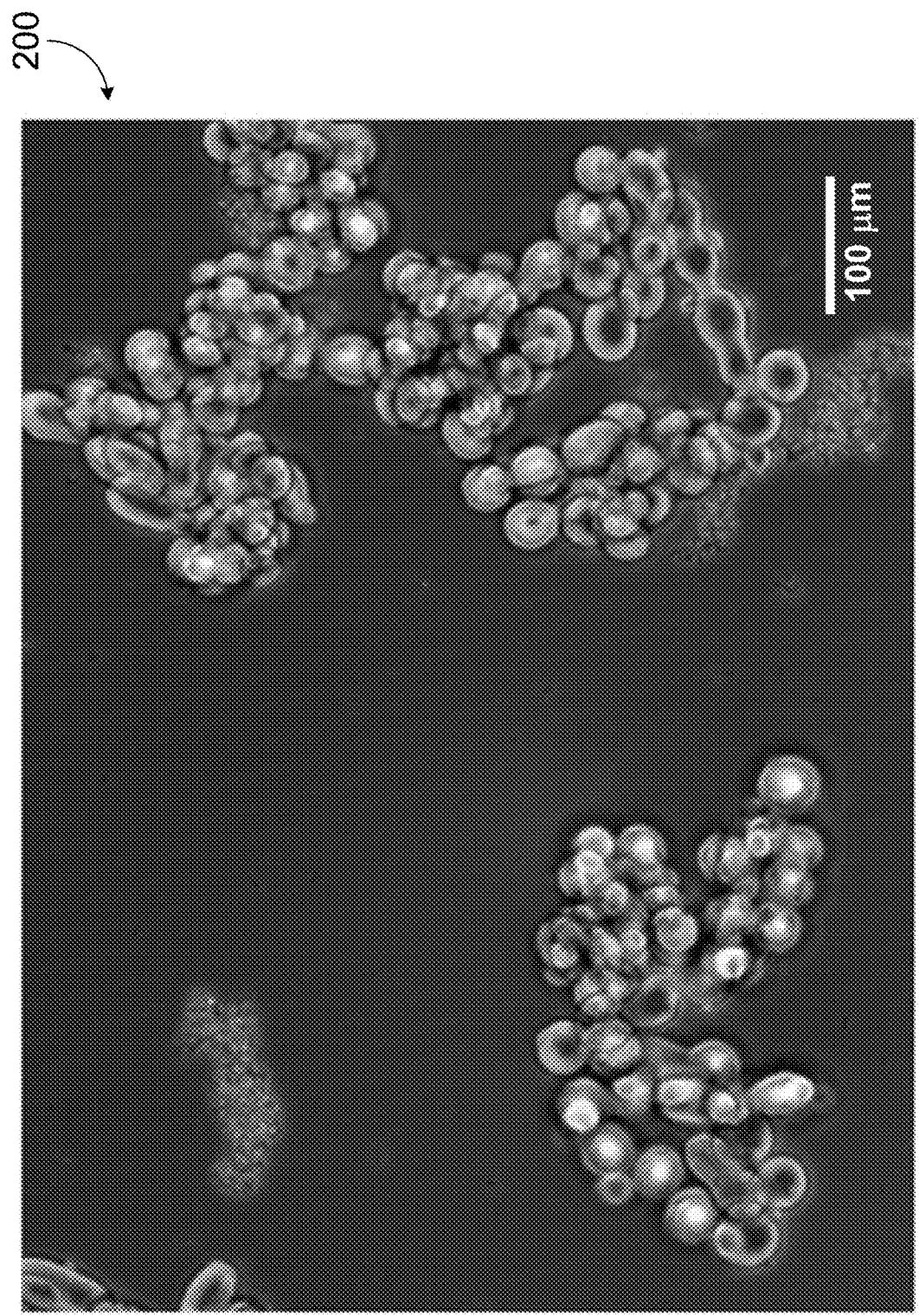
FIGS. 2-6 each show representations of gelatin microparticles for example support materials.
Figure 3:
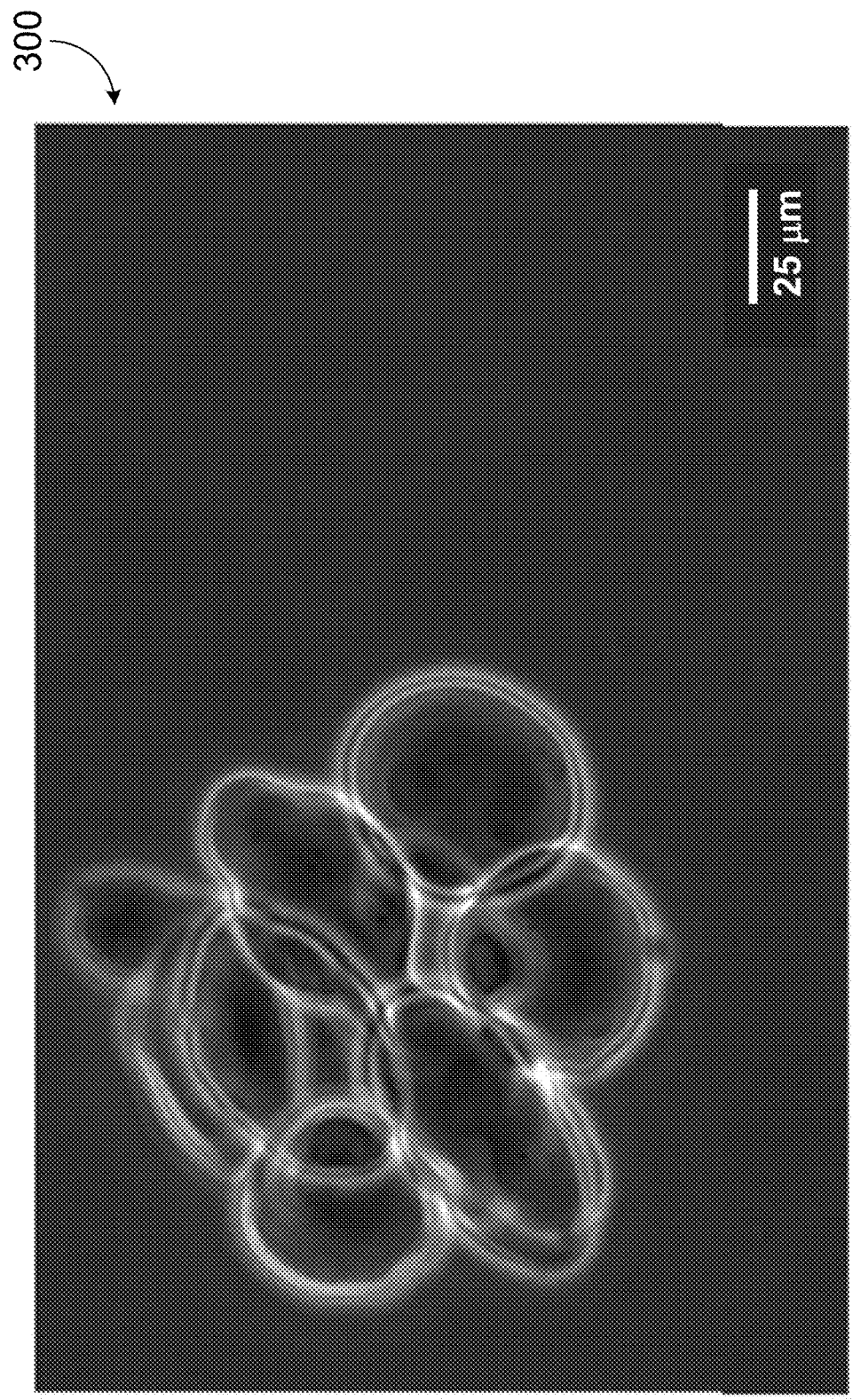

FIG. 2 shows an example of gelatin microparticles 200 formed by the coacervation process described above. The scale bar is 100 micrometers. FIG. 3 shows an example of gelatin microparticles 300 formed by the coacervation process described above. The scale bar is 25 micrometers. The microparticles have substantially the same geometry, including size, shape, etc.

The process of gelatin coacervation can be altered further by the addition of other charged polymers to the coacervate solution, otherwise known as complex coacervation. In a simple coacervate with a single polyampholyte polymer, the polymer's own charges perfectly neutralize at the isoelectric point. In a complex coacervate, charges between two separate polymers complex together.

Figure 4:
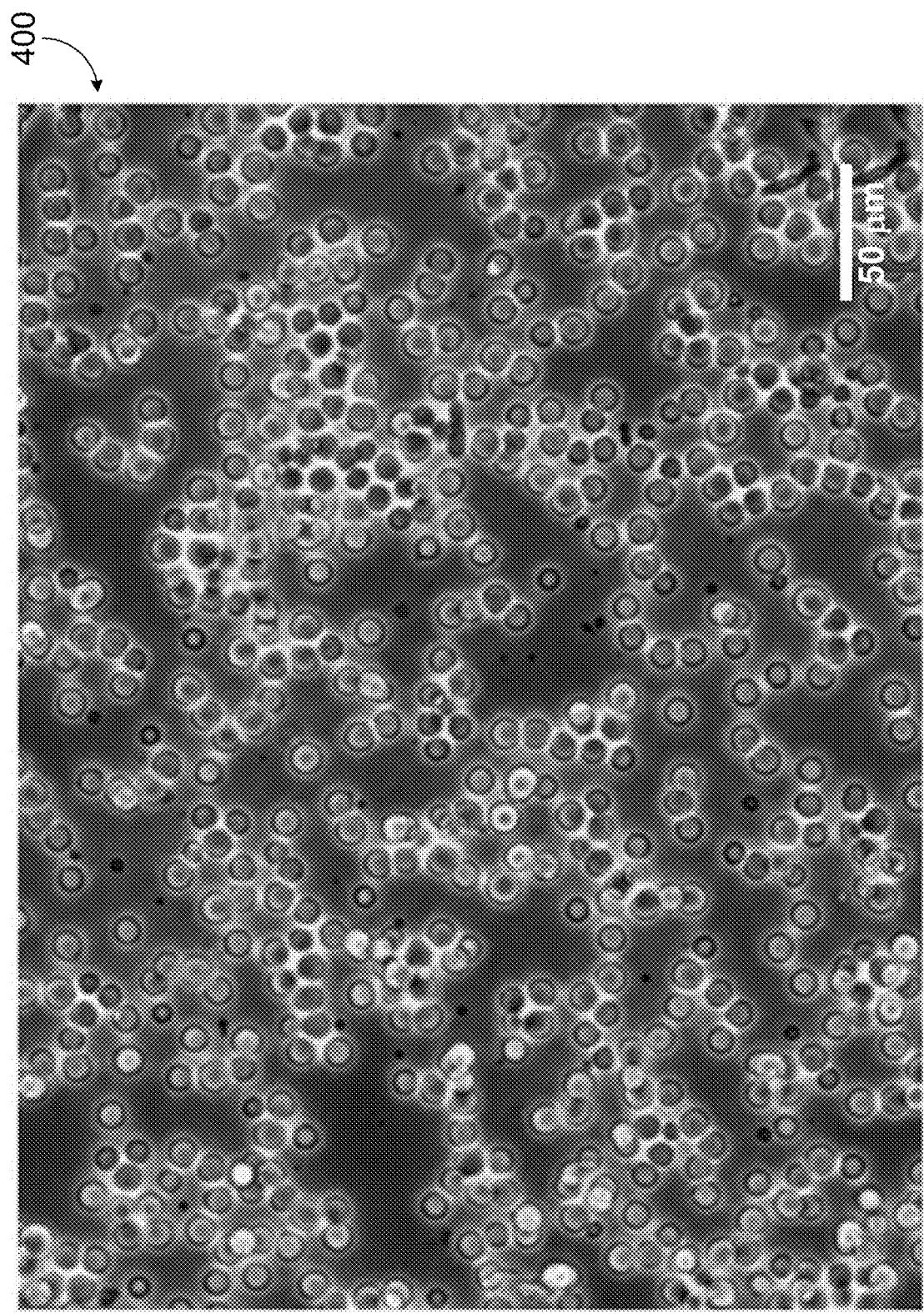

For example, FIG. 4 shows an example of gelatin microparticles 400 formed through complex coacervation. The addition of Gum Arabic allows for complex coacervation between the two polymers, producing microparticles with extremely consistent size, morphology and individuality. Gelatin is more positively charged in acidic solutions while Gum Arabic is negatively charged in any solution with a pH>2.2-3. As a result, these two polymers are optimal for complex coacervation and can be coacervated near gelatin's isoelectric point. In FIG. 4, the gelatin microparticles shown are created through complex coacervation from 2.0 wt % gelatin B, 0.1 wt % gum arabic. The scale bar is 50 micrometers.

As described above in relation to FIG. 2, stirring rate affects the size of gelatin particle formation by applying a higher shear force to particles while they are forming. Higher shear forces disrupt the formation of gelatin particles above a critical size by causing larger particles to become less stable. As a result, higher stirring rates produce smaller particles. Stirring at nearly four times the standard speed (e.g., a standard speed of 100 RPM) produced particles less than one-third the size. Rapidly stirring the coacervate reduced the average particle size from 42.85±13.89 µmm to 13.66±4.41 µm. This shows a variance of less than 35% for the sizes of the particles.

Figure 5:
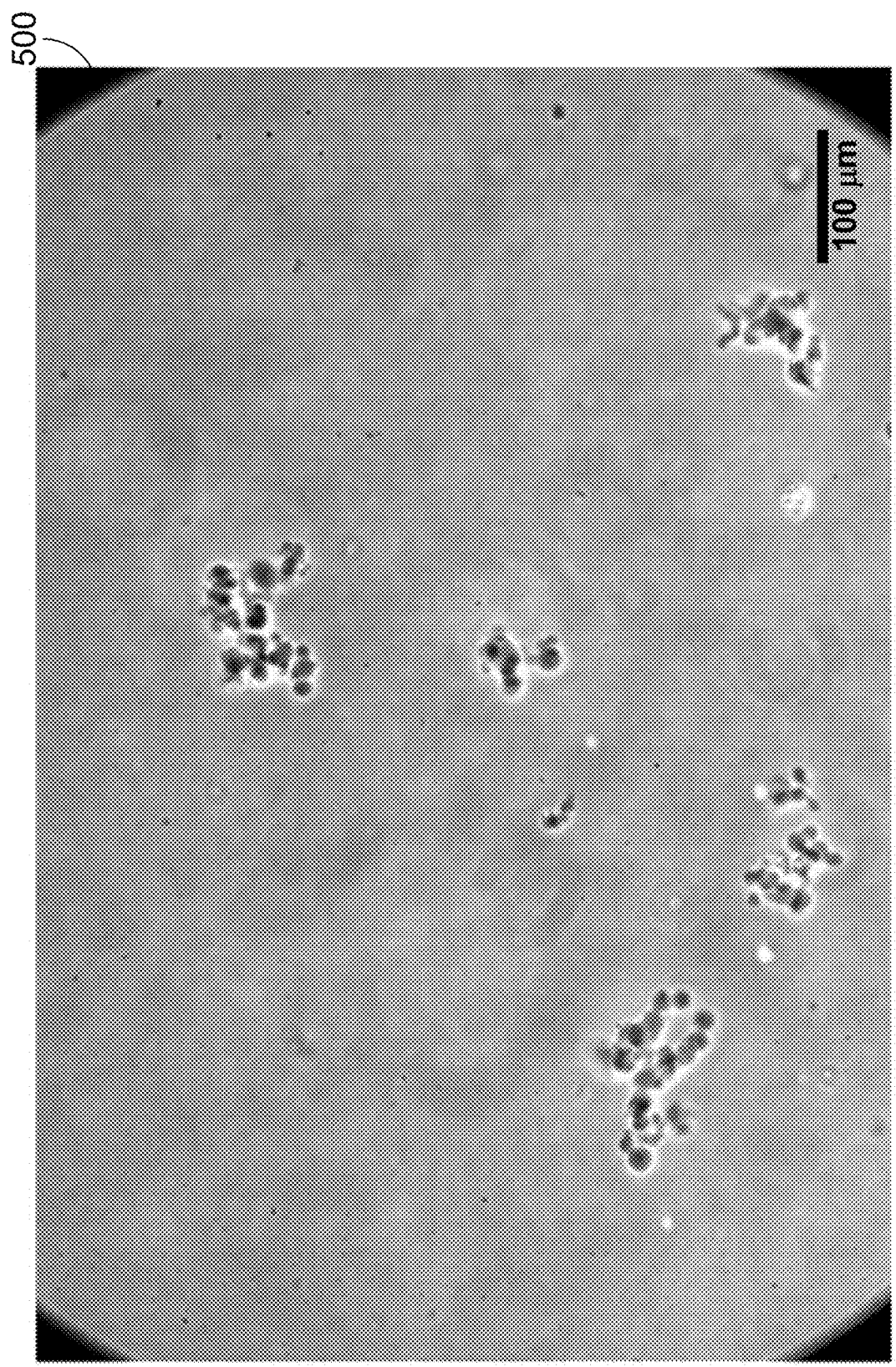

FIG. 5 shows examples of formations of smaller gelatin particles 500 relative to the gelatin microparticles 200, 300, and 400.

Varying other chemical parameters such as the solvent/non-solvent ratio can also be used to control particle size. The initial coacervation process used a 50:50 ratio of water to ethanol. Altering the ratio to 52.5:47.5 water to ethanol results in a decreased particle size of 6.42±1.68 µm and a narrower size distribution.

Figure 6:
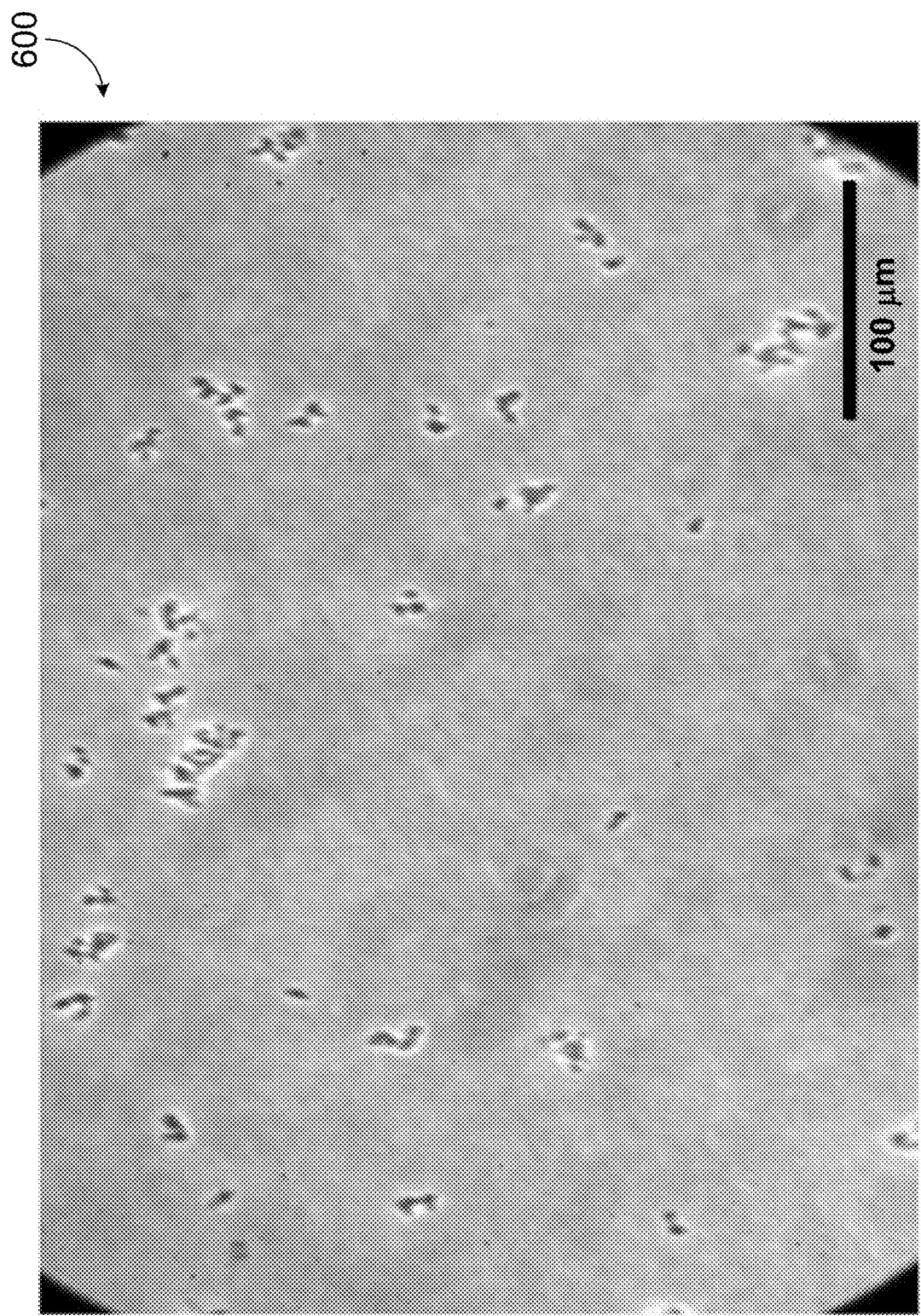
Figure 7:
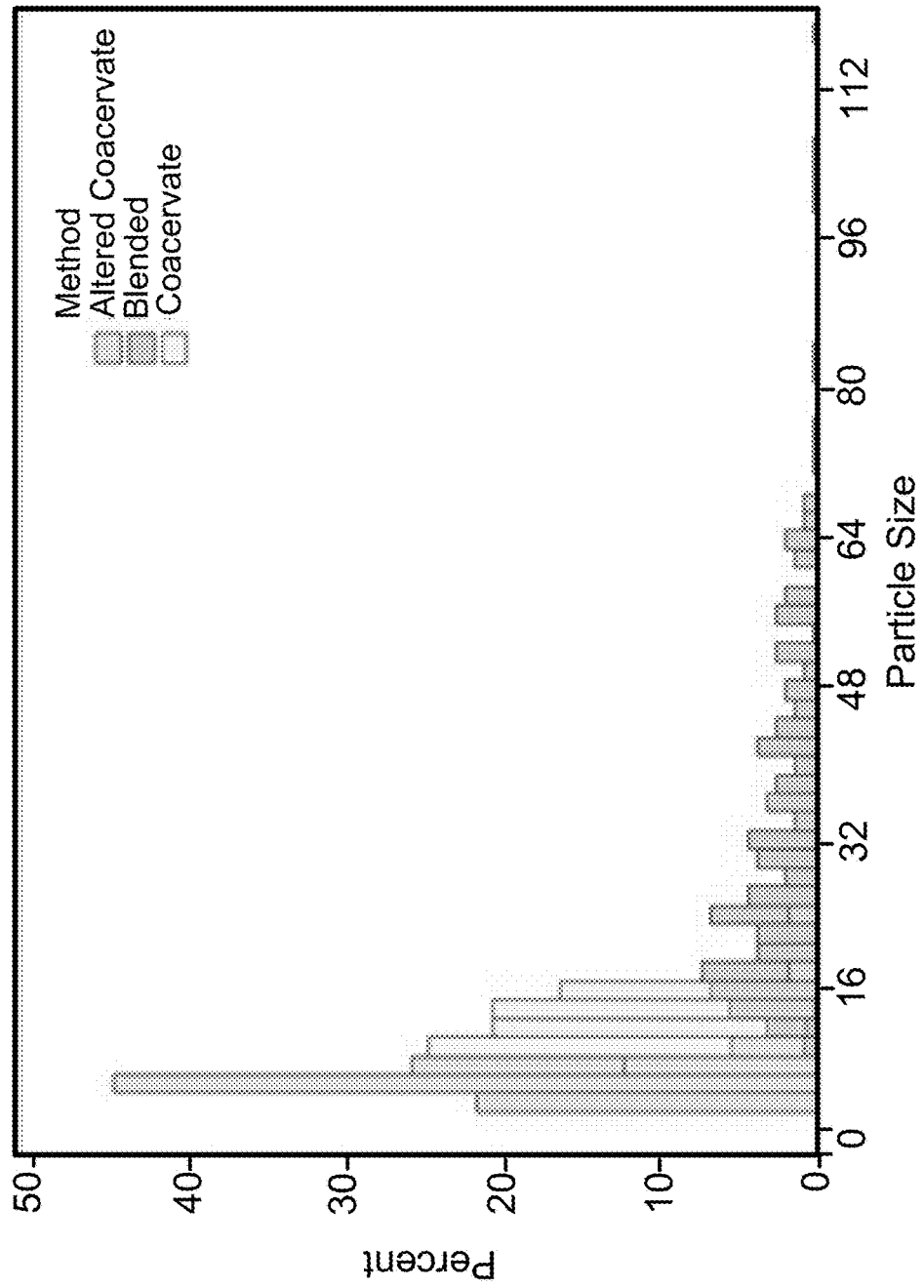
FIG. 7 shows a histogram of particle size distribution for an example support material.

For example, FIG. 6 shows gelatin particles 600 made from a 52.5:47.5 ratio of water to ethanol. The scale bar is 100 micrometers. Other ratios of water to ethanol can be used, such as 60:40 water to ethanol, 55:45, 50:50, etc. FIG. 7 shows a histogram of particle size distribution. Blended gelatin particles (labeled as blended) show a broadly distributed particle size. Particles from 50:50 water to ethanol coacervation (labeled as coacervate) show a narrower distribution of smaller particles. The 52.5:47.2 water to ethanol coacervation (labeled as altered coacervate) exhibits and even narrower size distribution of smaller particles (e.g., less than about 10 micrometers in diameter).

Figure 8:
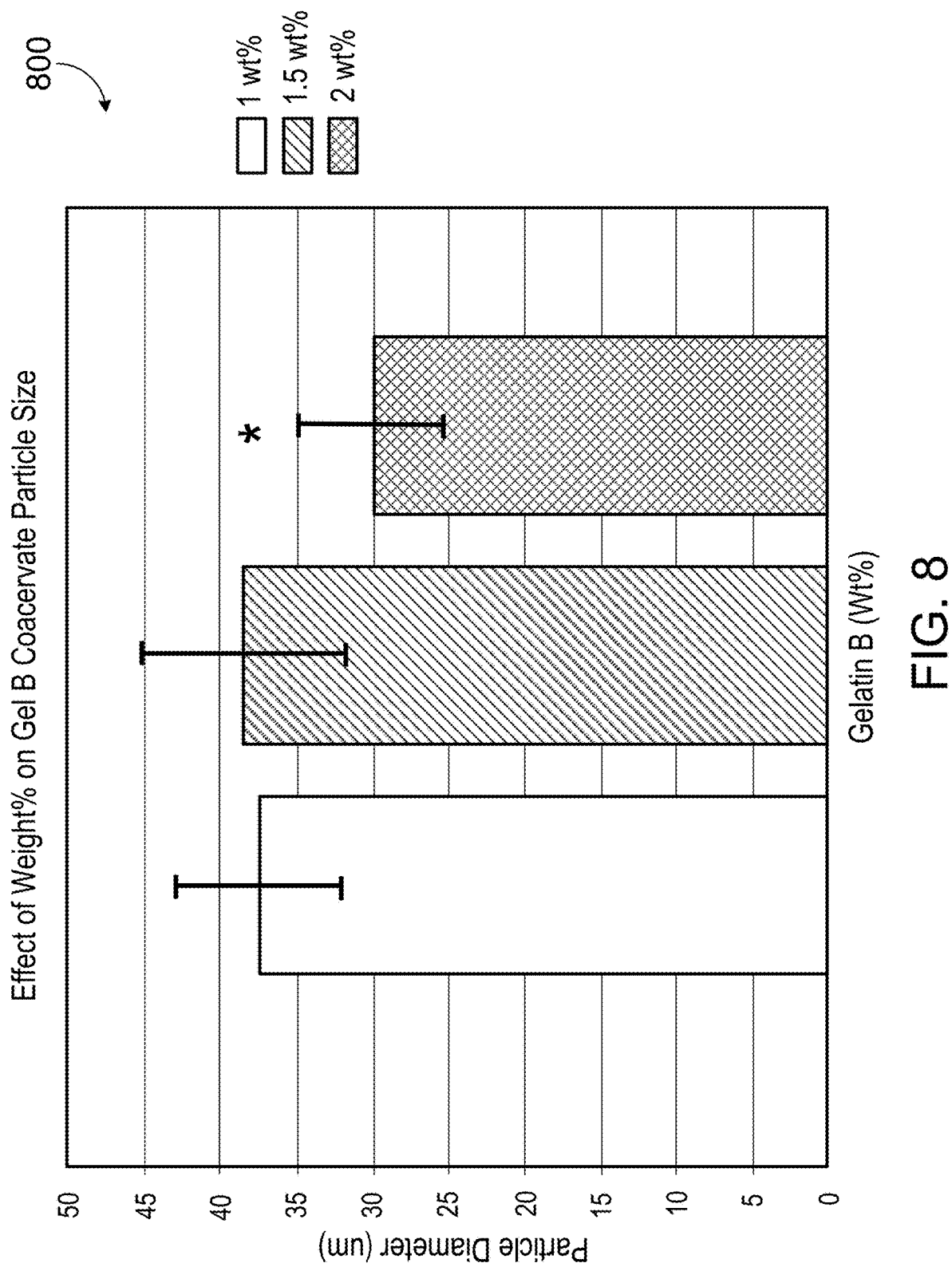
FIG. 8 shows a graph representing gelatin concentration against particle size for example support materials.

The average particle size remains consistent between varying weight percentages of gelatin when using the same manufacturing conditions. As long as the critical manufacturing conditions are consistent, increasing the weight percentage of gelatin increases the overall yield of particles from the coacervation process, not their morphology. FIG. 8 shows a graph 800. The graph 800 indicates that increasing the concentration of gelatin in the coacervation does not have a large effect on particle size (<10 microns). Several manufacturing conditions that affect particle size include bloom and processing method of a gelatin (e.g., acid-cured, lime-cured, etc.), pH of the coacervation solution, volume ratio of water to ethanol, use of surfactant (F127 Pluronic), cooling rate of the coacervate, and stirring rate of the coacervate. By controlling these conditions of the coacervation solution, the solubility of the gelatin (and particle geometry) is thereby controlled. Coacervation formation is highly dependent on controlling the solubility of gelatin between fluid and gel phases after the gelatin has been dissolved into solution. Lowering gelatin's solubility afterwards prevents the formation of a single matrix of gelatin and instead forms particles of gelatin as the solubility continues to decrease.

Gelatin bloom strength is dependent upon the average molecular weight of gelatin molecules. Higher molecular weight gelatin is less soluble in the water-ethanol solution than its lower weight counterparts and thus precipitates out of solution more readily. As the system cools and the solubility of gelatin decreases, gelatin molecules will precipitate out of solution in order of their molecular weight, starting with the highest. High bloom gelatin with a higher average molecular weight will therefore precipitate out of solution at different time points than a lower molecular weight gelatin, affecting the time point and temperature at which stable particles will form.

Animal tissues processed with an acid or base produce acidic (A) or basic (B) gelatin, respectively. These gelatins have different isoelectric points, making their solubility at certain pHs different. Adjusting the pH of the solution to a molecule's isoelectric point (pI) represents a minimum in solubility. At the isoelectric point, a gelatin molecule undergoes sequential charge neutralization with its own charged residues as well as those of other gelatin molecules, collapsing the molecules and bringing them out of solution. As a result, the pH of the coacervation solution also dictates the solubility of the gelatin and the formation of microparticles.

Gelatin is soluble in water and nearly insoluble in organic solvents such as alcohol. If gelatin is first dissolved in water at temperatures above its melting temperature and then cooled, gelatin forms a continuous gel. In a coacervation solution with a roughly 50:50 mixture of ethanol and water, gelatin becomes less soluble as alcohol associates more strongly with water as the temperature of the coacervation solution drops. As a result, gelatin cannot form a continuous matrix in a water-ethanol solution at lower temperatures due to its insolubility in alcohol. Controlling the ratio of water to ethanol in the coacervation solution greatly dictates the solubility of gelatin when forming a coacervate.

Figure 9:
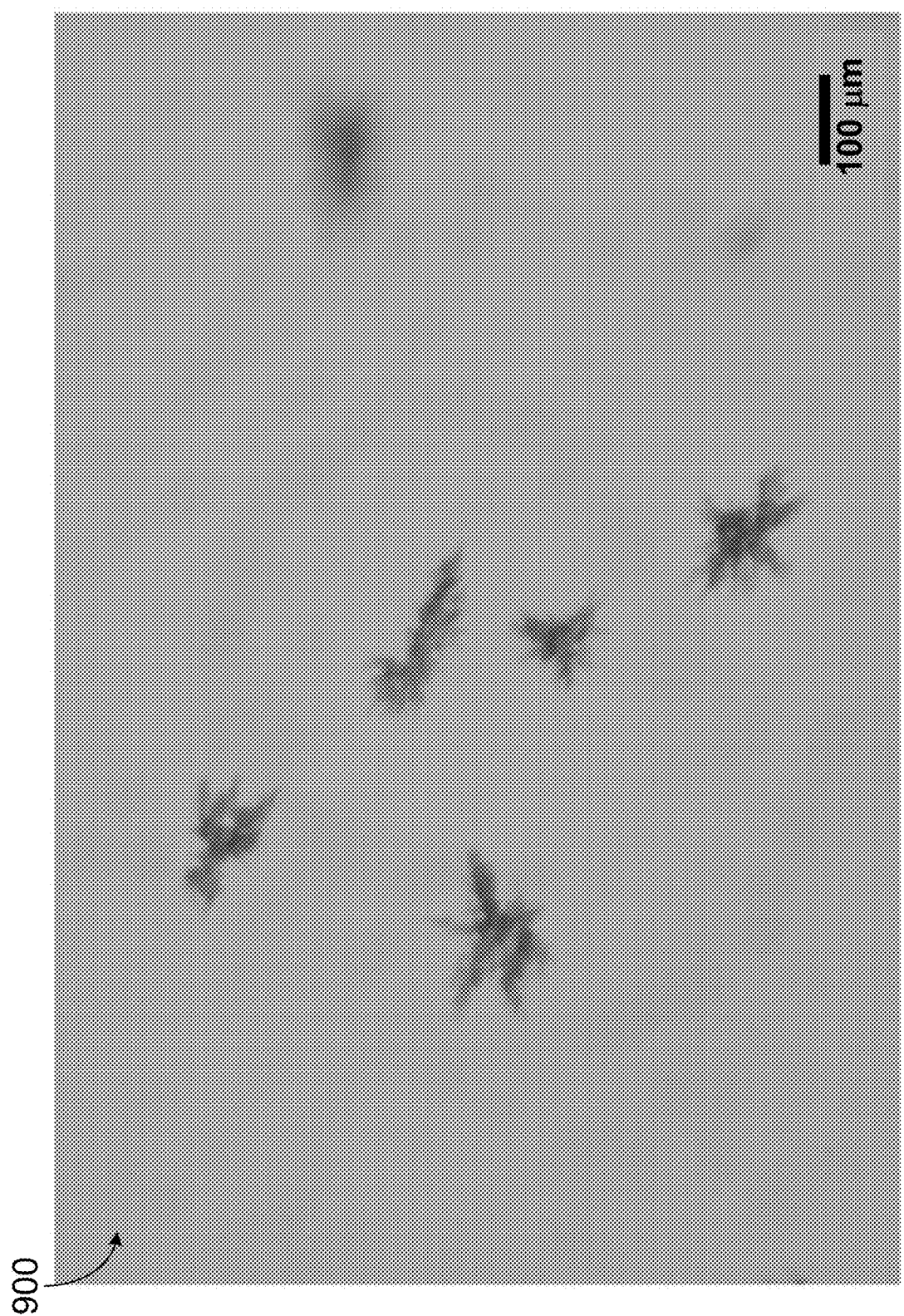
FIGS. 9-10 each show example support materials.

Use of a surfactant (e.g., F127 Pluronic) prevents the clumping of forming gelatin particles. Without a surfactant, gelatin particles tend to adhere to one another, forming large, rough, dendritic clumps, such as the particles 900 shown in FIG. 9. Use of a surfactant prevents or reduces the formation of these dendritic particles, resulting in the smooth, round particles, such as particles 200, 300, 400, 500, and 600 of FIGS. 2-6. FIG. 9 shows formation of large dendritic particles due to the absence of a surfactant. The scale bar is 100 micrometers.

Figure 10:
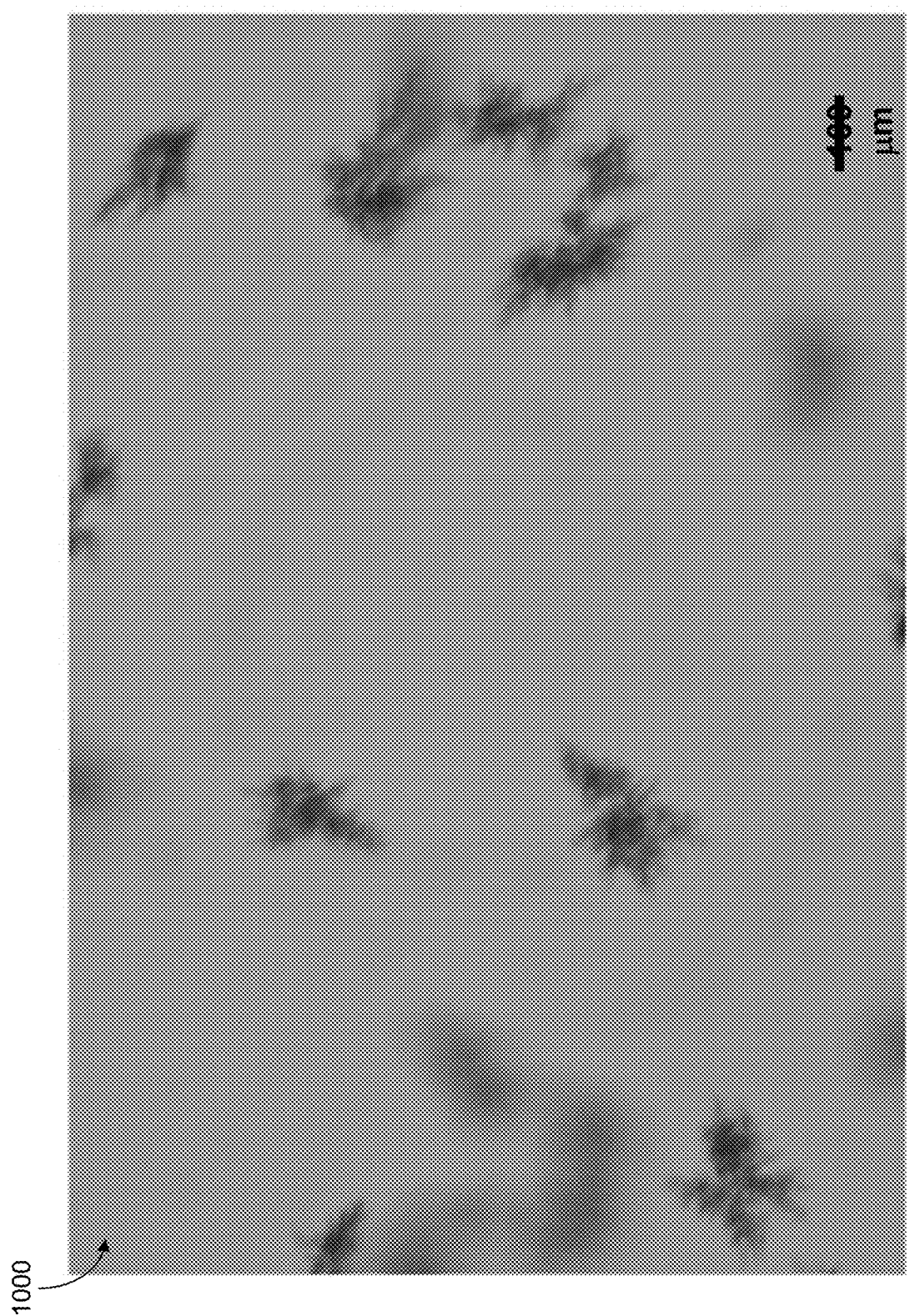

Rapidly cooling the coacervate solution promptly lowers the solubility of gelatin. Cooling the solution quickly (e.g., faster than 1° C./min) results in gelatin precipitating out of solution more rapidly. If gelatin precipitates out of solution too quickly, it cannot slowly adhere to existing gelatin particles, resulting in the rapid buildup of gelatin on a single particle and the formation of rough dendritic particles. FIG. 10 shows particles 1000. The particles 1000 are large and irregular dendritic particles 1000 compared to the particles of FIGS. 2-6. The particles 1000 form by rapidly cooling the coacervate solution with ice. The scale bar is 100 micrometers.

Controlling Hydration

Figure 11:
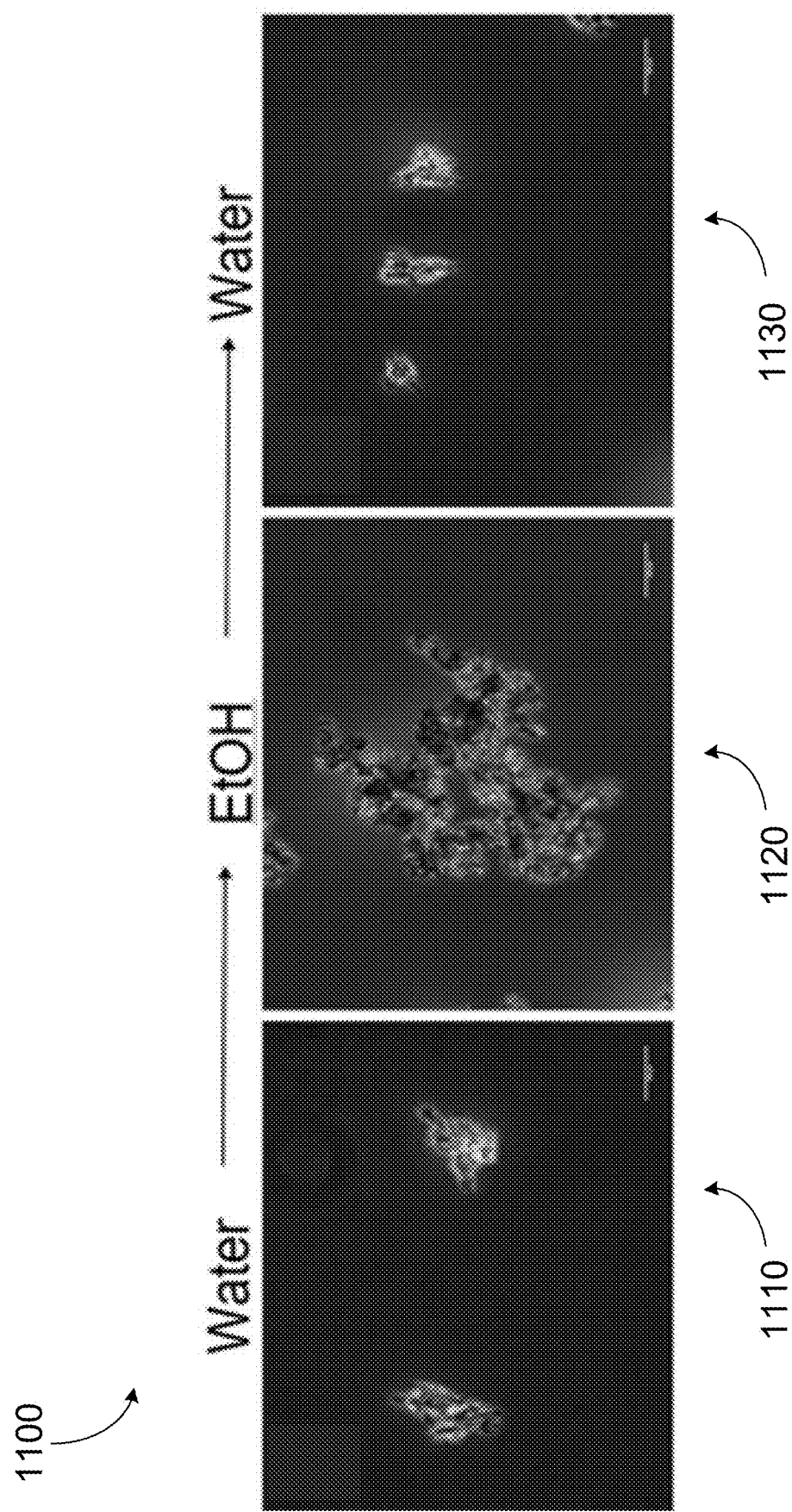
FIG. 11 shows examples of hydration processes for support materials.

FIG. 11 shows example processes 1100 for controlling particle hydration. Particle hydration can be manipulated by composition of the solution of the support material. Gelatin particles hydrate in accordance to osmotic pressure and pH. Utilizing the same dehydration principle in their formation, coacervate-derived gelatin particles can be dehydrated by transferring them from water, as particles 1110 are shown, into ethanol, shown by particles 1120. The hydrophilic gelatin particles 1120 agglomerate together in order to reduce their surface energy. Since gelatin is insoluble in ethanol, the particles 1120 are able to be stored in a dehydrated state, incapable of melting into solution. Storing the particles 1120 in ethanol also allows for storage below 0° C. without risking ice crystal formation in the support material. Transferring the gelatin slurry back into water rehydrates the particles 1130 and allows the particles 1130 to dissociate from one another. The dehydration/hydration process is repeatable and allows for the long-term storage of coacervate-derived gelatin particles in a dehydrated state that can be easily reversed to an original state.

Figure 12A:
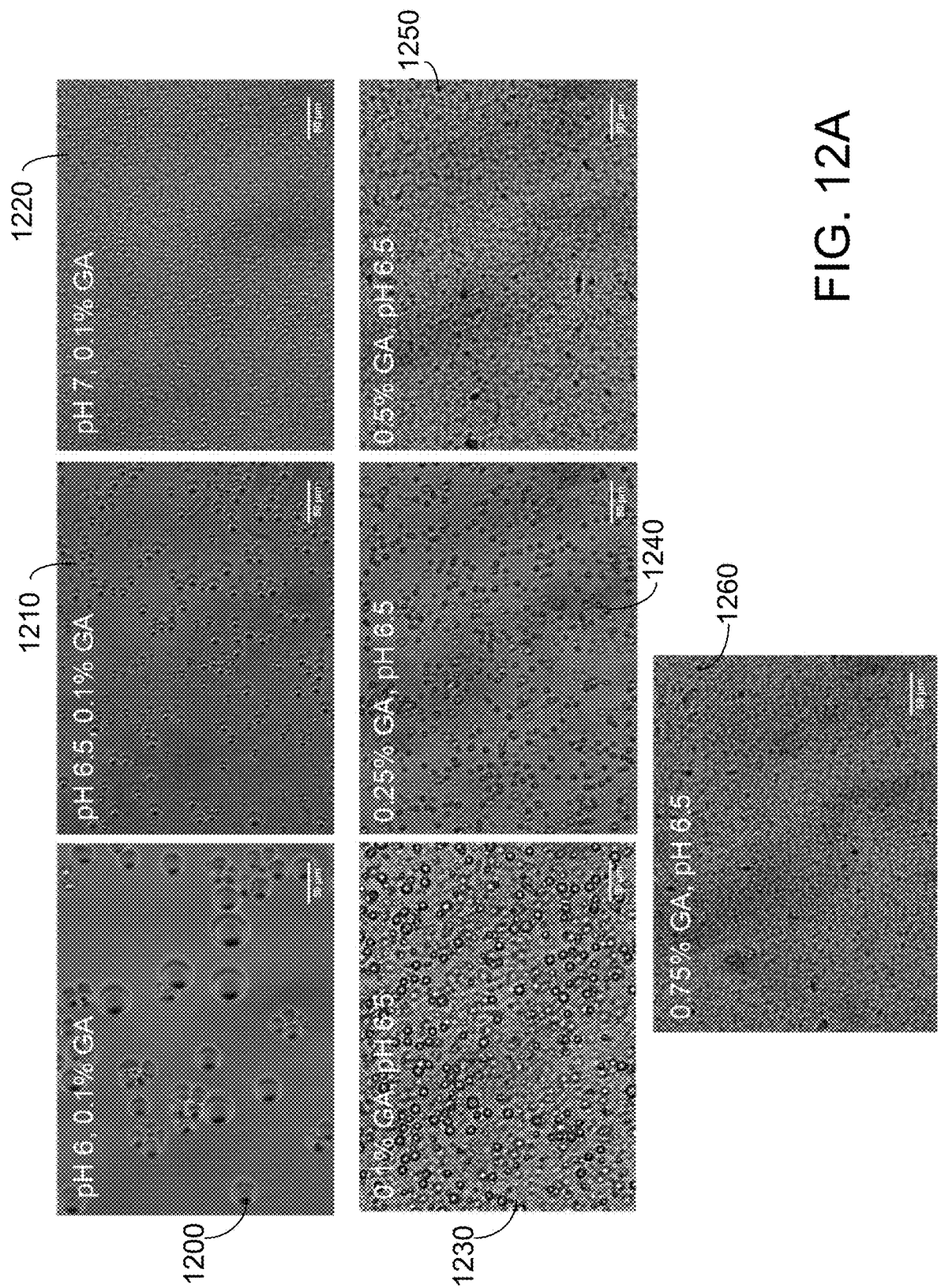
FIGS. 12A-12B show examples of particle size and yield control for a support material.

FIG. 12A shows examples of particles of a gelatin support material formed using varying pH values and varying gum arabic concentrations. For each example, the scale bar is 50 micrometers. Particles 1200 are formed with a solution pH of 6 and 0.1% concentration of gum arabic. Particles 1210 are formed with a solution pH of 6.5 and a 0.1% concentration of gum arabic. Particles 1220 are formed with a solution pH of 7 and a 0.1% concentration of gum arabic. Particles 1230 are formed with a solution pH of 6.5 and a 0.1% concentration of gum arabic. Particles 1240 are formed with a solution pH of 6.5 and a 0.25% concentration of gum arabic. Particles 1250 are formed with a solution pH of 6.5 and a 0.5% concentration of gum arabic. Particles 1260 are formed with a solution pH of 6.5 and a 0.75% concentration of gum arabic. As can be seen in FIG. 12A, particle size decreases when the solution pH moves away from the isoelectric point for gelatin (5-6 pH). As can be seen in FIG. 12A, particle size deceases as gum arabic concentration is increased. This is because there is an increase in nucleation sites in the concentration, and the same amount of gelatin is precipitating from the water/ethanol solution.

Figure 12B:
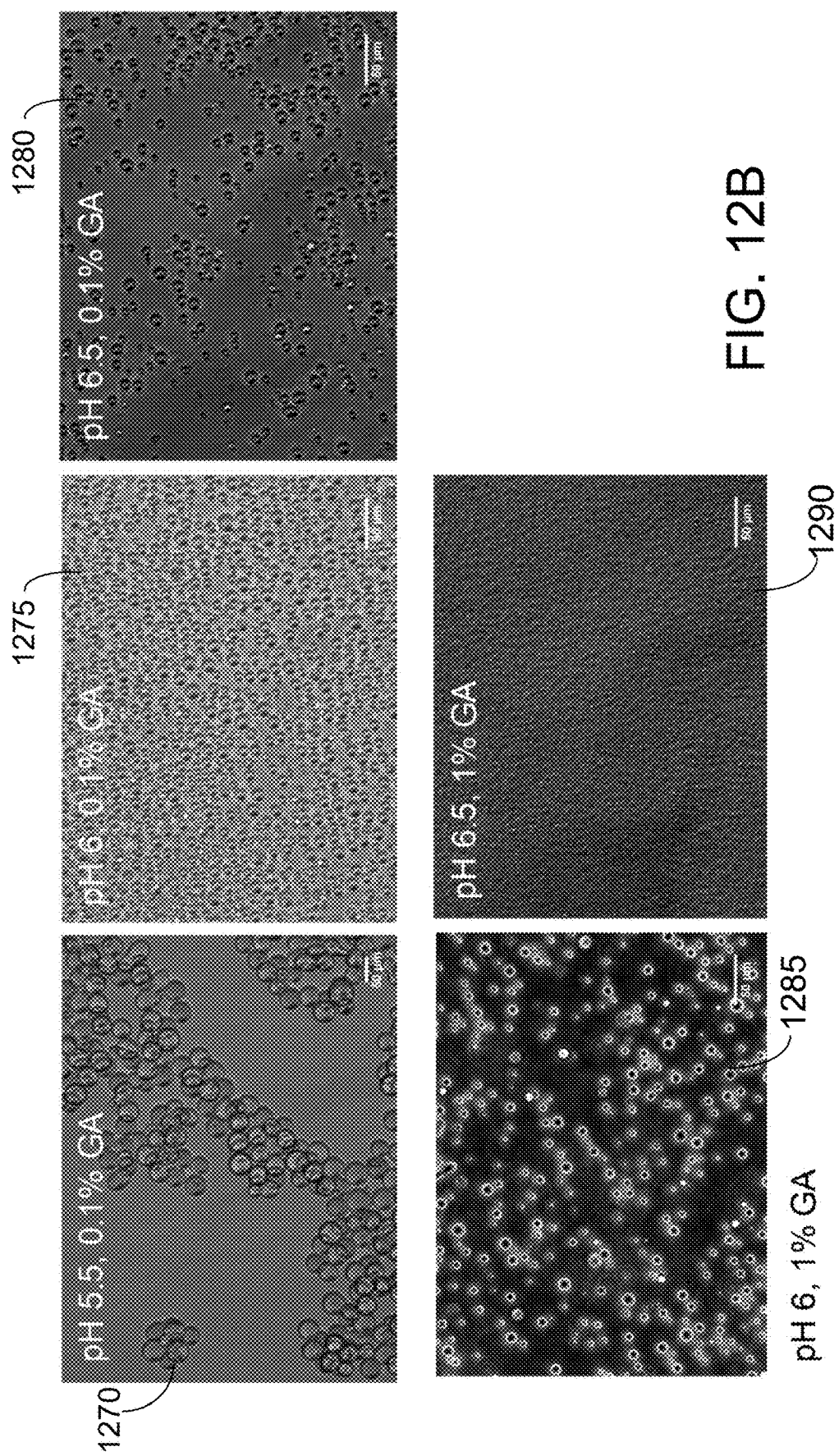

FIG. 12B shows examples of controlling size and yield of particles in the support material. Particles 1270 are formed with a solution pH of 5.5 and a 0.1% concentration of gum arabic. Particles 1275 are formed with a solution pH of 6.0 and a 0.1% concentration of gum arabic. Particles 1280 are formed with a solution pH of 6.5 and a 0.1% concentration of gum arabic. Particles 1285 are formed with a solution pH of 6 and a 1% concentration of gum arabic. Particles 1290 are formed with a solution pH of 6.5 and a 1% concentration of gum arabic. As seen in FIG. 12B, pH and gum arabic concentration can be tuned simultaneously to adjust particle size and slurry yield. A pH 6, 1% gum arabic concentration maintains a particle size of around 8-12 μm while yielding relatively more slurry for the support material. Comparing particle yield for roughly the same sizes, a pH 6, 1% gum arabic concentration yielded about 57.15 million particles/mL, and a pH 6.5, 0.1% gum arabic concentration yielded about 18.98 million particles/mL. If the gum arabic derived support material includes any debris, a brief centrifugation step can be used to remove these dense and generally large particles, while the rest is washed away prior to cell seeding.

Rheology

After compaction, the microparticles of the support material form a slurry that behaves as a yield-stress fluid. After a critical stress has been applied to the slurry, it begins to flow. Such behavior can be analyzed using a rheometer to deform a sample of slurry precisely and monitor its deformation in terms of parameters such as shear stress and shear rate to calculate viscosity. Yield-stress fluids show a constant instantaneous viscosity profile when undergoing stresses too low to initiate flow. This is due to yield-stress fluids behaving as a solid for stresses below the critical yield-stress required to initiate flow. Once the critical yield-stress has been reached the material quickly transitions from behaving like a solid to a fluid. At this level of applied stress, the material experiences a rapid decrease in viscosity with increasing shear rate, evidence of a deviation from the high instantaneous viscosity. The transition from solid to fluid behavior is initiated by a critical yield-stress being applied to the material in order to trigger particle movement. Below the critical shear stress, cohesive forces between particles is greater than the external shear forces being applied to them, resulting in stationary particles and a solid-like behavior. Particle movement is initiated at the critical yield-stress when the force applied to the particles overcomes the total cohesive force and particles begin to slip past one another. As a shear stress above the critical yield-stress is maintained, particles will continue to slide past one another and exhibit fluid-like behavior. When the shear force decreases below the critical yield-stress, particles re-adhere to one another by the same forces that initially held them together.

Figure 13:
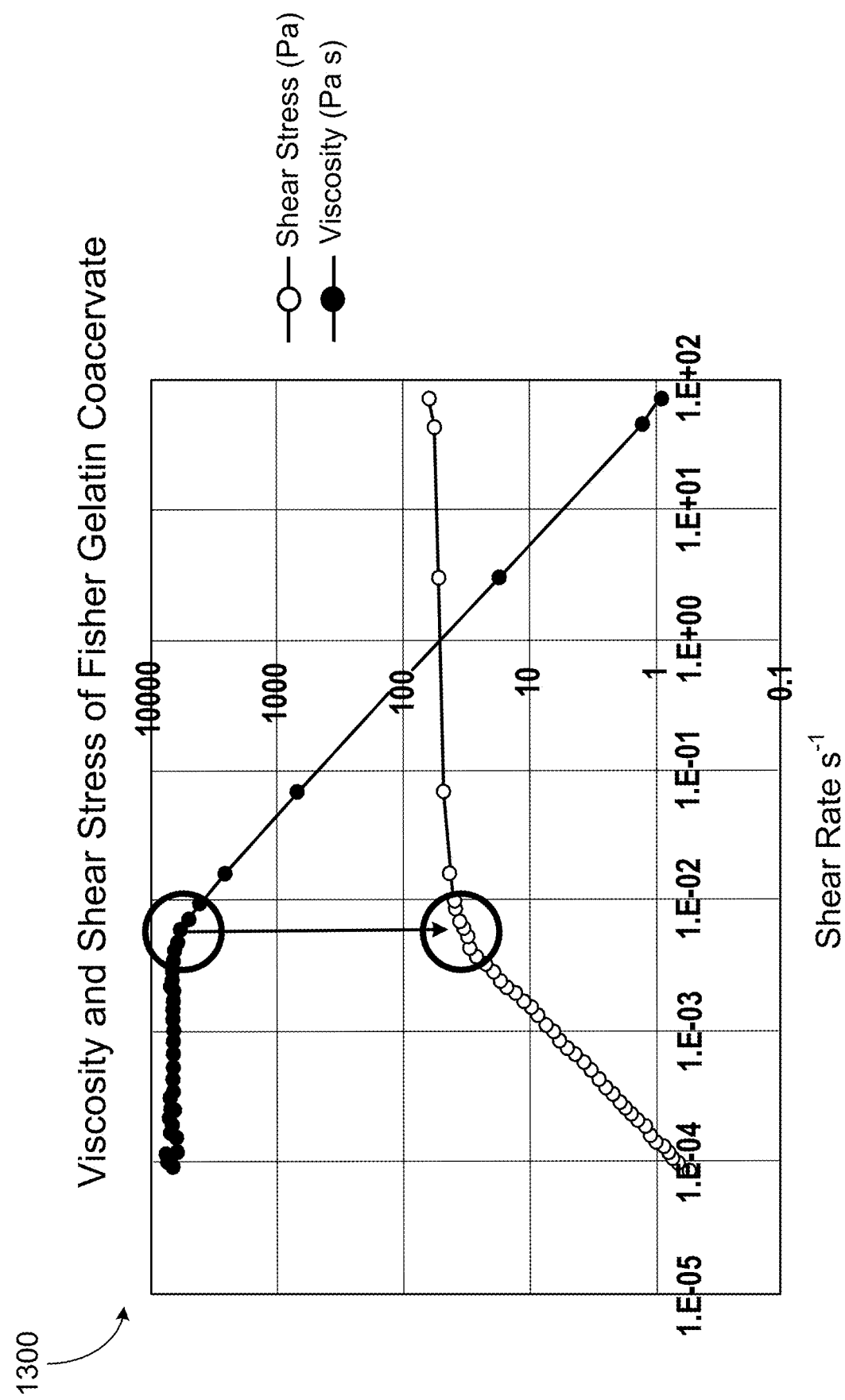
FIGS. 13-15 show example rheology data of the support material.

FIG. 13 shows a graph 1300 of yield-stress properties for a support material produced from coacervate as described above. If left to deform for longer times, the material's viscosity eventually begins to level off at a much lower viscosity as it reaches the viscosity of its fluid-like state at high shear stresses. The viscometry data can be taken from a sample of gelatin microparticle slurry produced by the outlined coacervation process. In FIG. 13, circles indicate the moment the critical yield-stress is applied, resulting in the rapid drop in sample viscosity, confirming the support exhibits shear thinning behavior.

The deviation from the continuous region of the viscosity can be associated with an instantaneous shear stress needed to initiate flow of the Bingham plastic fluid. Additional rheological tests such an amplitude sweep and frequency sweep can more precisely determine the linear viscoelastic region (LVR) and yield-stress of a non-Newtonian fluid, respectively. The LVR is determined from the linear region of the elastic modulus (G'). A strain from the LVR is then chosen to perform a frequency sweep, which for this sample was chosen to be 0.035.

Figure 14:
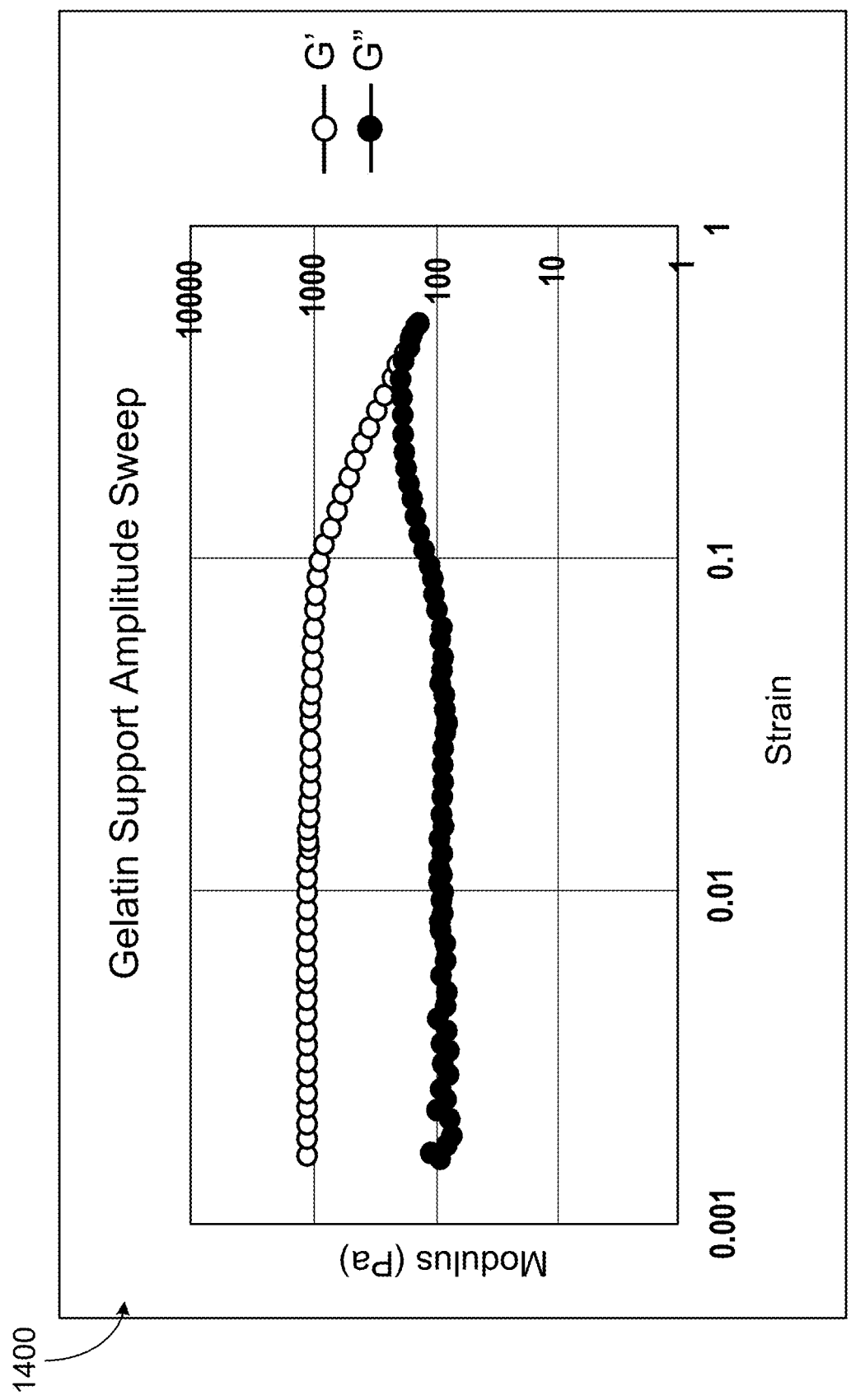
Figure 15:
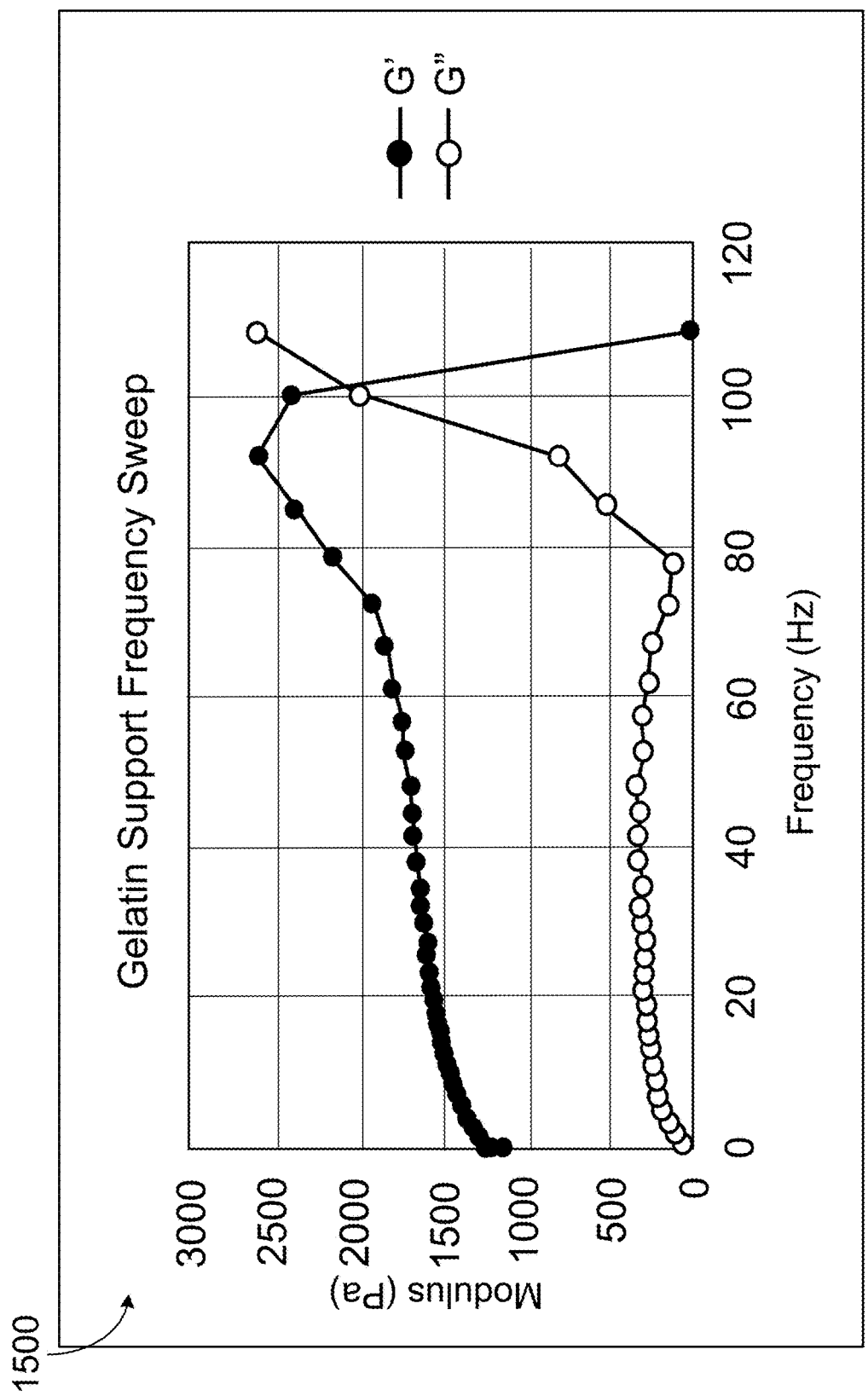

FIG. 14 shows an example graph 1400 of amplitude sweep data of a gelatin support material. The linear plateau of the elastic storage modulus (G') indicates the LVR from which a strain for a frequency sweep can be chosen. FIG. 15 shows an example graph 1500 of frequency sweep data of a gelatin support material. The elastic storage modulus (G') and viscous loss modulus (G") are measured. The intersection point indicates a frequency at which the support material yields and transitions from behaving as an elastic solid to a viscous fluid. The intersection point thus corresponds to the yield-stress of the support material.

The yield-stress of this slurry has been shown to be alterable through the compaction step of centrifugation. Higher centrifugation forces force the particles together, thereby compacting them. The yield-stress of the slurry can be tuned by altering the degree of compaction of the particles by changing these centrifugation forces. As a higher G-force further compacts the slurry, the slurry's yield-stress increases. This behavior can be seen across various brands of gelatin that were used to create microparticle slurry via the coacervation process outlined above.

Figure 16:
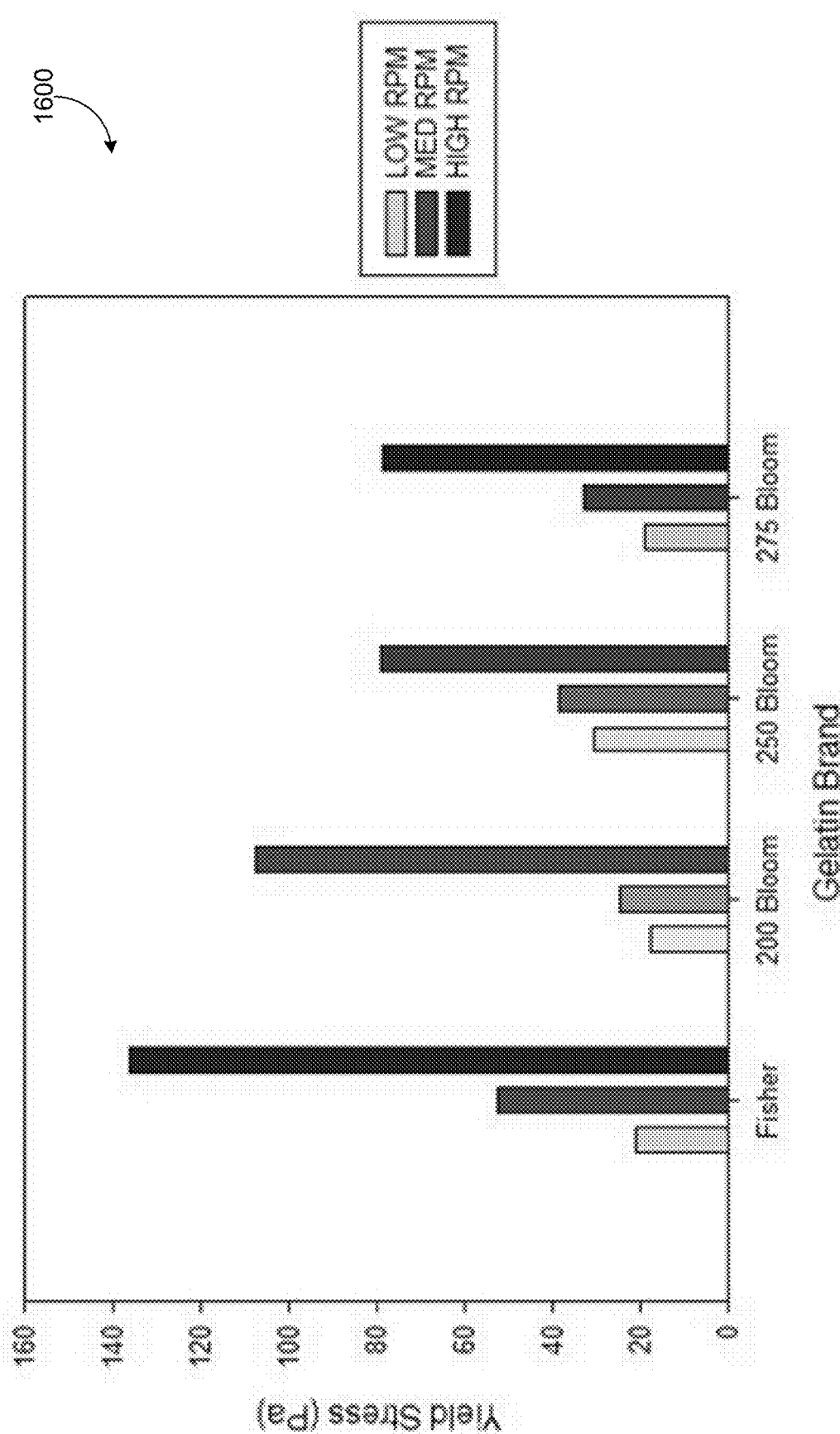
FIG. 16 shows yield-stress values for example support materials.

FIG. 16 shows a graph 1600 of example yield-stresses for support materials that were centrifuged at different speeds, or RPM. Slurries were centrifuged with a final centrifugation speed that was either "Low" (1100 RPM=227 G), "Medium" (2000 RPM=751 G), or "High" (4500 RPM=3803 G) and had their yield-stresses measured using the rheometer. The yield-stresses of various brands of gelatin are shown in FIG. 16. As RPM speed of centrifugation increases, the sample yield-stress increases across all types of gelatin, regardless of a bloom value of the gelatin. Controlling the yield-stress of the support broadens the spectrum of materials that can be used with the slurry. Tuning the slurry's yield-stress allows for a broader range of ink compatibility by more closely matching the viscosity of the ink with the viscosity and yield-stress of the support. The precision of printing increases when the viscosity of the ink is similar to the viscosity and the yield-stress of the support, relative to a lower precision of embedded printing in a support material with a different viscosity and yield-stress.

Increasing FRESH 3D Print Fidelity

Since coacervate-derived microparticles can form a Bingham Plastic fluid, they can be utilized in FRESH printing. One of the limits to extrusion accuracy and precision in FRESH printing is the size and shape distribution of the particles in the sacrificial support bath. Irregular particle size and shape (such as the particles of FIG. 1B) prevents consistent extrusion and leads to lower print fidelity. When support material is removed, the particles act as porogens, leaving void defects behind in the print (FIG. 17B).

Since coacervate-derived gelatin particles are both smaller and more consistent in size and shape relative to gelatin particles produced from prior techniques (e.g., a blending technique, emulsion technique, etc.), extrusion accuracy and precision is increased and void defects in prints are smaller. The result is a significant increase in print fidelity. To demonstrate this, a "window frame" model is sliced and pathed using standard 3D printing software.

Figure 17:
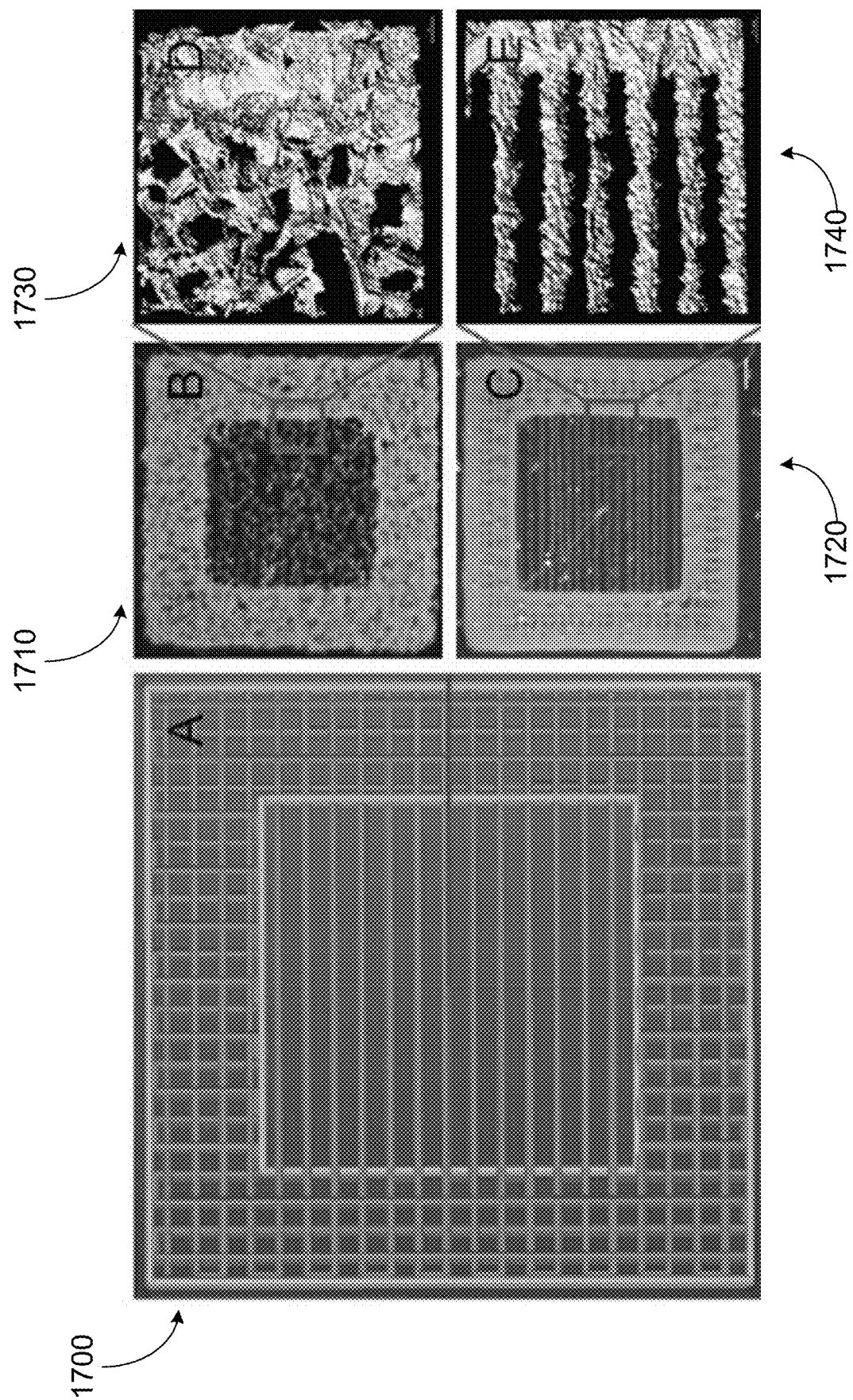
FIG. 17 shows stages of an additive manufacturing process that uses example support materials.

FIG. 17 shows an example of high print fidelity using the support materials described herein, relative to lower print fidelity of prior support materials. Image 1700 shows a model of a 3D printed mesh. Using a collagen ink, the model is then printed into a blended support bath, shown in image 1710, and a coacervate-derived gelatin particle bath, shown in image 1720. Confocal images of labeled collagen ink highlight the increased feature resolution for collagen printed in coacervate support in image 1740 in comparison to one printed in a blended support bath in image 1730. The collagen structure printed in the coacervate support material has fewer voids and more regular structure compared to the collagen structure printed in the blended support material.

Since coacervation is a scalable chemical process, large volumes of gelatin support can be created more efficiently than mechanical blending. This enables larger FRESH prints to be produced more rapidly and with less labor. The large prints (e.g., structures) still benefit from the improvements made to FRESH printing fidelity on the sub-millimeter scale shown in FIG. 17. The result is the ability to print objects on the macro scale with higher fidelity than before.

Figure 18:
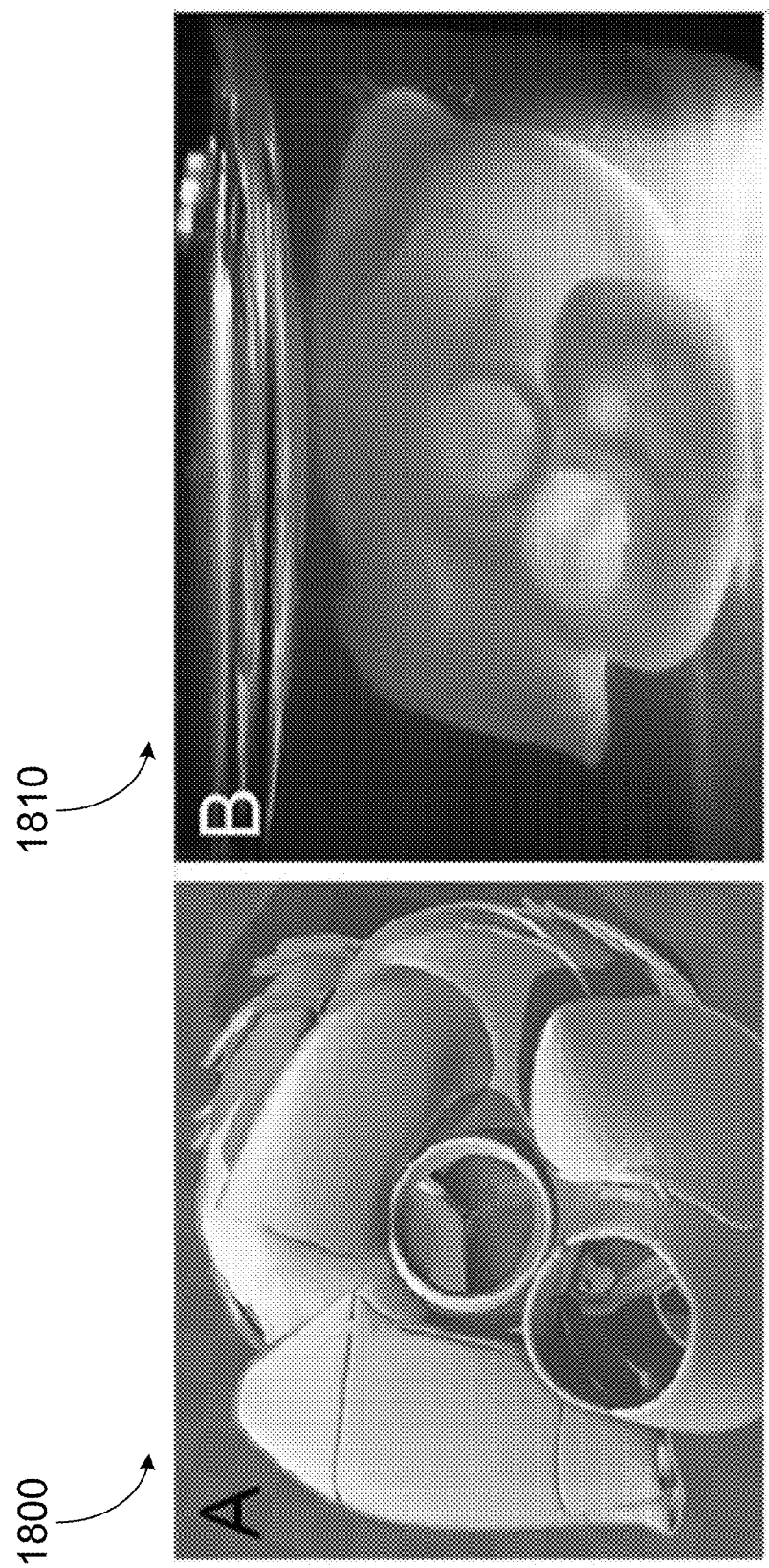
FIG. 18 shows an example print generated in an example support material.

FIG. 18 shows an example of a high-fidelity structure printed using the support material described herein. An adult heart model taken from patient-specific Mill data was converted into a 3D-printable format, shown in image 1800. A to-scale version of this heart model was then FRESH printed out of pure, unmodified, bovine collagen, shown in FIG. 1810.

Figure 19:
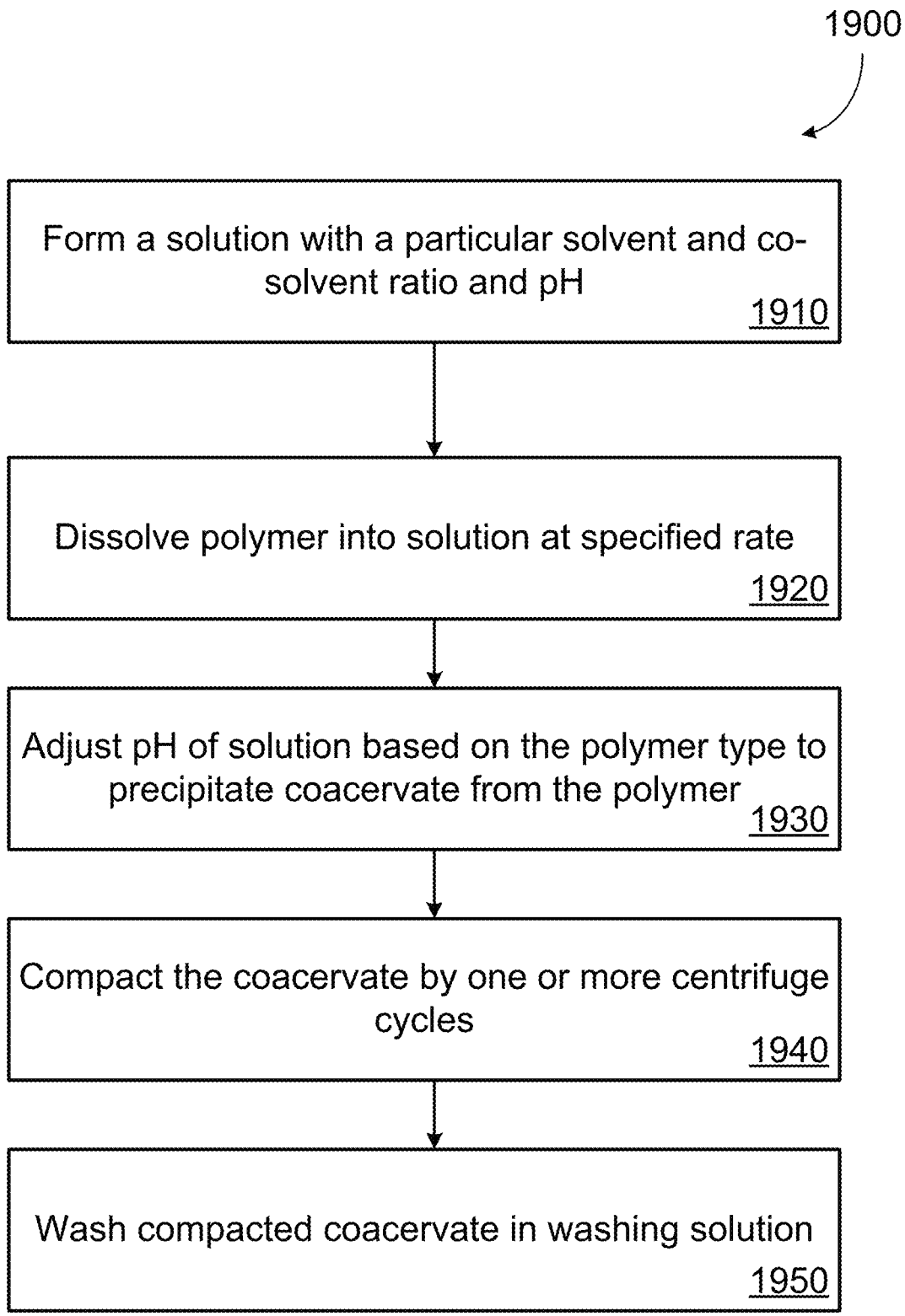
FIG. 19 shows a flow diagram of an example process for forming the support material.

FIG. 19 shows a flow diagram 1900 of an example process for producing the support material. A solution is formed (1910) with a particular solvent and co-solvent ratio and a particular pH. After selection of a polymer (e.g., gelatin, alginate, fibrin, etc.), the polymer is dissolved (1920) into the solution at a specified rate. The pH is adjusted (1930) based on the polymer type to precipitate coacervate from the polymer. The coacervate is compacted (1940) during one or more centrifuge cycles. The coacervate is washed (1950) in a washing solution which is chosen based on the type of polymer in the coacervate.

A number of embodiments have been described. Nevertheless, it will be understood that various modifications may be made without departing from the spirit and scope of the claims. Accordingly, other embodiments are within the scope of the following claims.

What is claimed is:

1. A support material for additive manufacturing comprising:
   a slurry comprising:
      a solution; and
      coacervate particles in the solution, the coacervate particles being of substantially uniform geometries;
   wherein at least a portion of the slurry forms a rigid body when experiencing a stress below a threshold stress;
   wherein a value of the threshold stress is based on the substantially uniform geometries of the coacervate particles; and wherein at least a portion of the slurry forms a viscous fluid when experiencing a stress above the threshold stress.

2. The support material of claim 1, wherein the solution comprises a surfactant configured to inhibit dendrite formation in the solution.

3. The support material of claim 1, wherein the coacervate particles each comprises at least one of gelatin, alginate, and cellulose.

4. The support material of claim 1, wherein the coacervate particles comprise two or more different polymers.

5. The support material of claim 4, wherein one of the two or more different polymers comprises gum arabic, and wherein another of the two or more different polymers comprises gelatin.

6. The support material of claim 1, wherein the solution comprises of water as a solvent and ethanol as a co-solvent, and wherein the solution comprises a ratio of the solvent to the co-solvent in a range of 30:70 and 70:30.

7. The support material of claim 1, wherein a mean size of the coacervate particles is between about 0.5 µm and about 60 µm.

8. The support material of claim 1, wherein a mean size of the coacervate particles varies less than about 35%.

9. The support material of claim 1, wherein the threshold stress comprises a critical shear stress in which a cohesive force between first and second of the coacervate particles of the slurry is approximately equal to an external shear force applied to the coacervate particles of the slurry.

10. The support material of claim 9, wherein a value of the critical shear stress is between about 10 Pa and about 10000 Pa.

11. The support material of claim 9, wherein a value of the critical shear stress is based on a viscosity of an ink for additive manufacturing in the slurry.

12. The support material of claim 11, wherein the ink comprises collagen.

13. A method for forming a support material for additive manufacturing, the method comprising:
generating coacervate from a polymer, the coacervate comprising particles that are substantially uniform in geometry, wherein generating the coacervate comprises:
forming a solution of a solvent and a co-solvent;
stirring the solution and dissolving the polymer into the solution; and
adjusting a pH of the solution to a particular value based on a type of the polymer; and
forming, from the coacervate, a slurry with a particular yield-stress value based on the coacervate comprising particles that are substantially uniform in geometry, the forming comprising compacting the coacervate during one or more centrifugation cycles.

14. The method of claim 13, further comprising:
selecting one or more parameters, and
modulating the one or more parameters during generation of the coacervate, each of the one or more parameters comprising:
a gelatin bloom value, a polymer processing method, a polymer precipitation rate, a polymer solubility, a molecular weight of the polymer, a polymer concentration, a volume ratio of the solvent and the co-solvent, a surfactant type, a surfactant concentration, a cooling rate, or a stirring rate.

15. The method of claim 13, further comprising:
selecting one or more parameters; and
modulating the one or more parameters during the forming of the slurry, the one or more parameters comprising:
a type of a washing solution, a centrifugation time of the one or more centrifugation cycles, a centrifugation force of the one or more centrifugation cycles, and a number of the one or more centrifugation cycles.

16. The method of claim 13, further comprising adding a surfactant to the solution.

17. The method of claim 13, further comprising dehydrating the slurry in ethanol.

18. The method of claim 17, further comprising rehydrating the slurry in water, wherein the slurry maintains the particular yield-stress value after dehydration and rehydration.

19. The method of claim 13, wherein the polymer is a first polymer, and wherein generating the coacervate further comprises:
adding a second polymer to the solution,
selecting an isoelectric point of either the first polymer or the second polymer, and
adjusting the pH based on the selected isoelectric point.

20. The method of claim 13, further comprising adjusting the one or more centrifugation cycles to cause the particular yield-stress value of the slurry to be a specified value.

21. The support material of claim 1, wherein the coacervate particles are approximately monodisperse in the solution.

22. A support material for additive manufacturing comprising:
a gelatin slurry comprising:
a colloid solution comprising ethanol and water;
a surfactant; and
coacervate microparticles in the colloid solution, the coacervate microparticles being monodisperse in the solution, the coacervate microparticles having mean sizes between 0.5-60 micrometers and a variance of size of less than 35%;
wherein at least a portion the slurry forms a rigid body when experiencing a shear stress below a yield-stress value;
wherein the yield-stress value is based on the mean sizes of the coacervate microparticles; and
wherein at least a portion of the slurry forms a viscous fluid when experiencing a shear stress above the yield-stress value.

* * * * *